United States Patent
Li et al.

(10) Patent No.: US 11,571,222 B2
(45) Date of Patent: Feb. 7, 2023

(54) NEUROSURGICAL ULTRASONIC FOCUSING ASSISTED THREE-STAGE ATOMIZATION COOLING AND POSTOPERATIVE WOUND FILM FORMING DEVICE

(71) Applicant: QINGDAO UNIVERSITY OF TECHNOLOGY, Qingdao (CN)

(72) Inventors: Changhe Li, Qingdao (CN); Min Yang, Qingdao (CN); Yiliang Yang, Qingdao (CN); Yali Hou, Qingdao (CN); Dongzhou Jia, Qingdao (CN); Yanbin Zhang, Qingdao (CN); Xiaowei Zhang, Qingdao (CN)

(73) Assignee: QINGDAO UNIVERSITY OF TECHNOLOGY, Qingdao (CN)

( * ) Notice: Subject to any disclaimer, the term of this patent is extended or adjusted under 35 U.S.C. 154(b) by 1084 days.

(21) Appl. No.: 16/098,277

(22) PCT Filed: Feb. 2, 2018

(86) PCT No.: PCT/CN2018/075018
§ 371 (c)(1),
(2) Date: Nov. 1, 2018

(87) PCT Pub. No.: WO2019/100588
PCT Pub. Date: May 31, 2019

(65) Prior Publication Data
US 2020/0254282 A1    Aug. 13, 2020

(30) Foreign Application Priority Data

Nov. 21, 2017  (CN) ........................... 201711165587.1
Nov. 21, 2017  (CN) ........................... 201721569020.6

(51) Int. Cl.
*A61B 17/16* (2006.01)
*A61F 13/02* (2006.01)
(Continued)

(52) U.S. Cl.
CPC ...... *A61B 17/1695* (2013.01); *A61F 13/0276* (2013.01); *A61F 13/12* (2013.01);
(Continued)

(58) Field of Classification Search
CPC . A61B 17/16; A61B 17/1613; A61B 17/1615; A61B 17/1626; A61B 17/1628;
(Continued)

(56) References Cited

U.S. PATENT DOCUMENTS 5,624,393 A * 4/1997 Diamond ............... A61B 17/14
604/289
6,443,969 B1 * 9/2002 Novak ........... A61B 17/320068
606/169

(Continued)

FOREIGN PATENT DOCUMENTS

| CN | 101966661 A | 2/2011 |
|---|---|---|
| CN | 102029551 A | 4/2011 |

(Continued)

OTHER PUBLICATIONS

Aug. 1, 2018 International Search Report issued in International Patent Application No. PCT/CN2018/075018.
(Continued)

*Primary Examiner* — Eric S Gibson
(74) *Attorney, Agent, or Firm* — Oliff PLC

(57) ABSTRACT

A neurosurgical ultrasonic focusing assisted three-stage atomization cooling and postoperative wound film forming device has a transducer housing and a nozzle, wherein a horn is arranged in the transducer housing, at least two layers of piezoelectric ceramic sheets are arranged at the top of the
(Continued)

Figure 1:
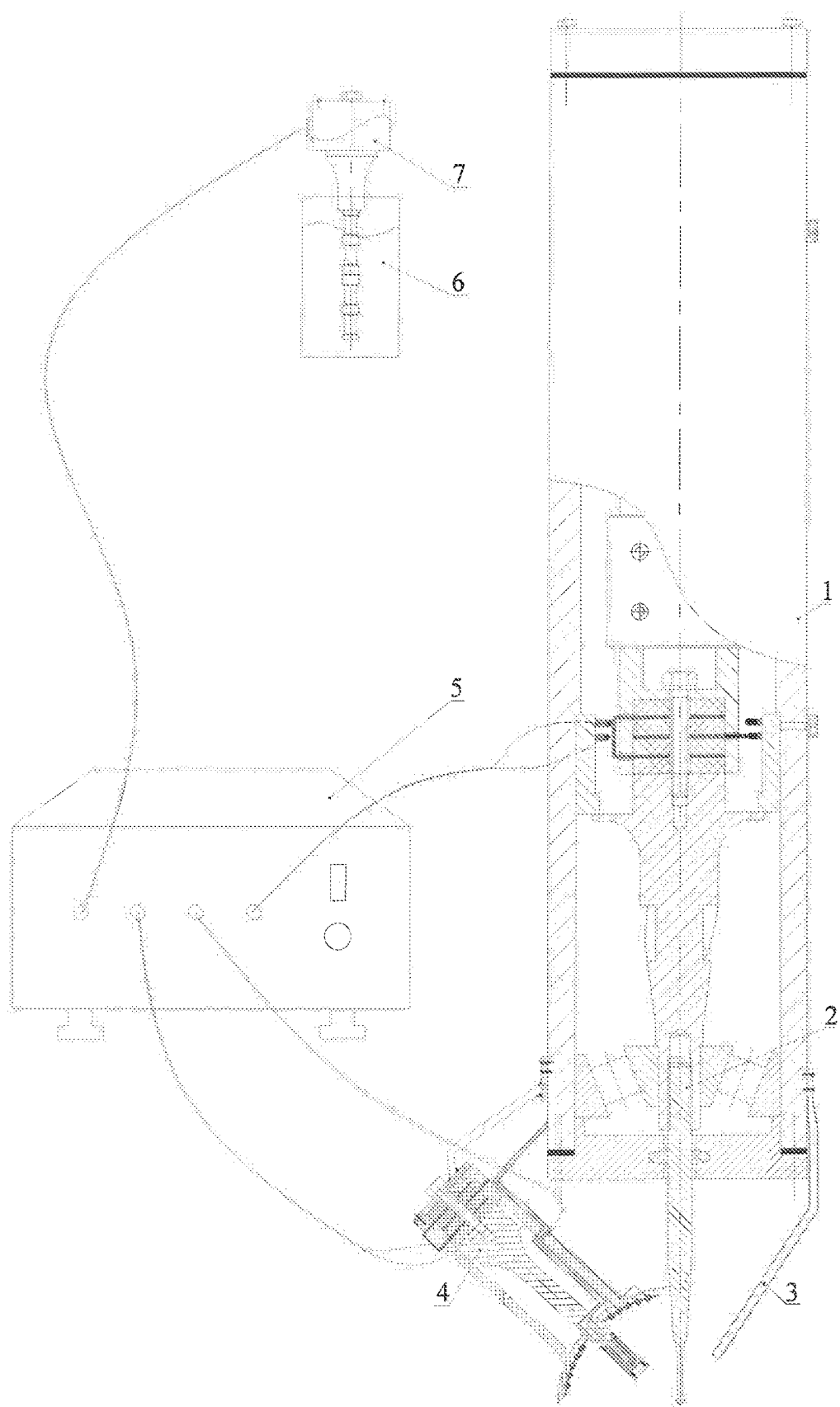
Figure 2:
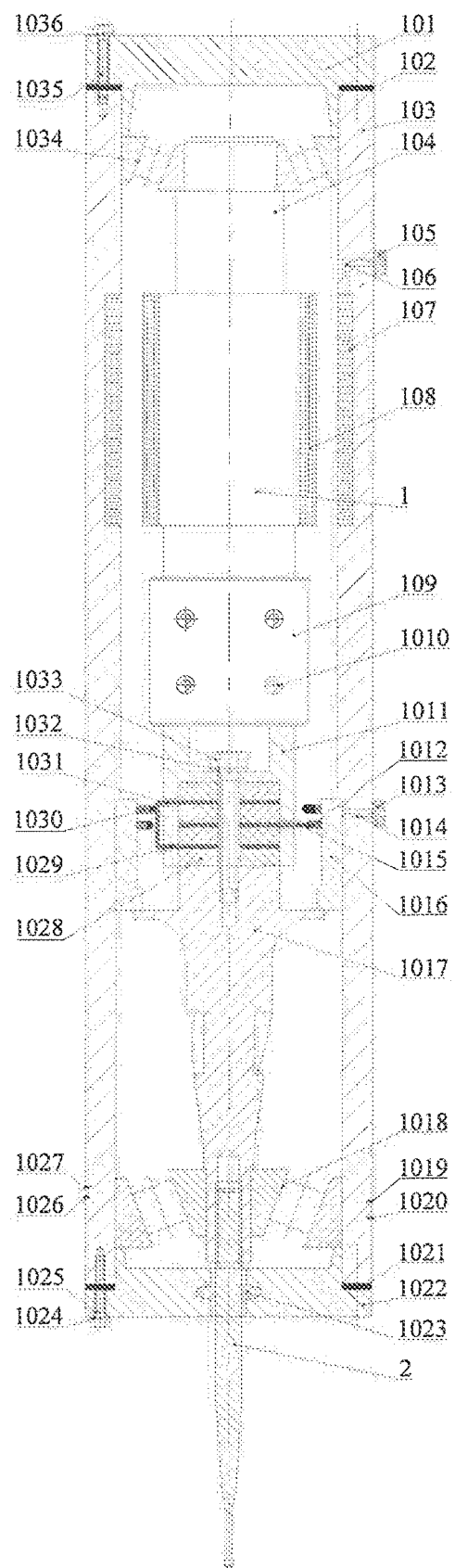

horn, an electrode sheet connected with an ultrasonic generator is arranged between two adjacent layers of piezoelectric ceramic sheets, the bottom of the transducer housing is of a hemispherical structure, and a plurality of piezoelectric elements connected with the ultrasonic generator are arranged inside the hemispherical structure; and the nozzle is arranged at the bottom of the horn and connected with a medical nanofluid storage cup, compressed gas can also be introduced into the nozzle, and an electrode is also arranged inside the nozzle.

10 Claims, 10 Drawing Sheets

(51) Int. Cl.
    *A61F 13/12*     (2006.01)
    *A61B 17/00*     (2006.01)

(52) U.S. Cl.
    CPC ............... *A61B 2017/00296* (2013.01); *A61B 2017/1651* (2013.01); *A61B 2017/1653* (2013.01); *A61B 2217/007* (2013.01)

(58) Field of Classification Search
    CPC ............ A61B 17/1644; A61B 17/1695; A61B 2017/1651; A61B 2017/1653
    See application file for complete search history.

(56) References Cited

U.S. PATENT DOCUMENTS

| | | | | |
|---|---|---|---|---|
| 8,316,961 | B2* | 11/2012 | Isobe | B23B 39/14 |
| | | | | 606/139 |
| 8,573,090 | B2* | 11/2013 | Isobe | B25J 13/00 |
| | | | | 901/41 |
| 9,119,640 | B2* | 9/2015 | Shimokita | A61B 18/22 |
| 11,406,397 | B2* | 8/2022 | Li | A61B 17/1622 |
| 2010/0011923 | A1* | 1/2010 | Suda | C10M 169/04 |
| | | | | 451/7 |
| 2011/0319879 | A1* | 12/2011 | Shimokita | A61B 18/22 |
| | | | | 606/16 |
| 2012/0031219 | A1* | 2/2012 | Isobe | B23B 39/14 |
| | | | | 74/490.04 |
| 2012/0043100 | A1* | 2/2012 | Isobe | A61B 17/1631 |
| | | | | 901/41 |
| 2017/0333053 | A1* | 11/2017 | Li | A61B 17/16 |
| 2019/0150955 | A1* | 5/2019 | Li | A61B 17/1633 |
| 2020/0254282 | A1* | 8/2020 | Li | A61F 13/12 |
| 2022/0054161 | A1* | 2/2022 | Mayer | A61B 90/94 |

FOREIGN PATENT DOCUMENTS

| | | | | |
|---|---|---|---|---|
| CN | 102212892 | A | 10/2011 | |
| CN | 101773893 | B | 3/2012 | |
| CN | 101773894 | B | 6/2012 | |
| CN | 101932877 | B | 1/2013 | |
| CN | 203096243 | U | 7/2013 | |
| CN | 103084981 | B | 11/2014 | |
| CN | 105105819 | A | 12/2015 | |
| CN | 105154614 | A | 12/2015 | |
| CN | 105350088 | A | 2/2016 | |
| CN | 205020304 | U | 2/2016 | |
| CN | 103590132 | B | 3/2016 | |
| CN | 205146560 | U | 4/2016 | |
| CN | 105581983 | A | 5/2016 | |
| CN | 104324839 | B | 8/2016 | |
| CN | 104826755 | B | 1/2017 | |
| CN | 206334172 | U | 7/2017 | |
| CN | 107789029 | A | 3/2018 | |
| CN | 105728254 | B | 4/2018 | |
| CN | 105964473 | B | 8/2018 | |
| JP | 2010207409 | A * | 9/2010 | ......... A61B 17/1695 |
| JP | 2010246701 | A * | 11/2010 | ......... A61B 17/1633 |
| JP | 2010260139 | A * | 11/2010 | ......... A61B 17/1631 |

OTHER PUBLICATIONS

Aug. 1, 2018 Written Opinion of the International Searching Authority issued in International Patent Application No. PCT/CN2018/075018.

* cited by examiner

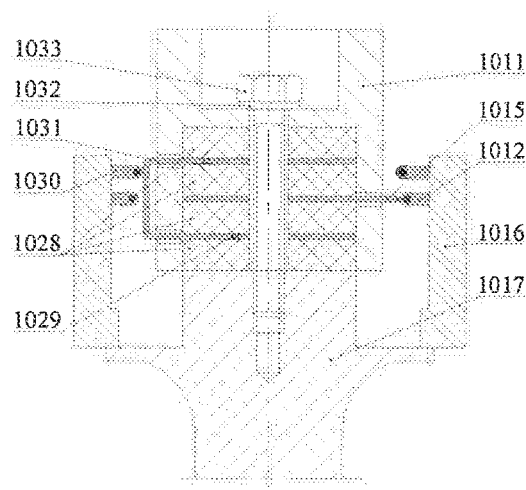
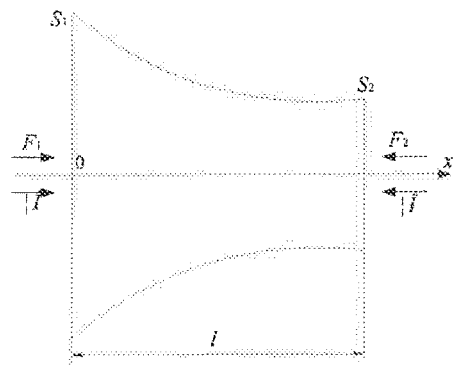
Fig. 3    Fig. 4
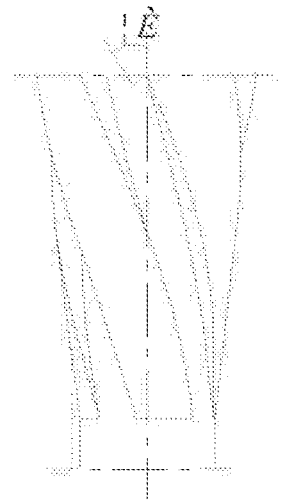
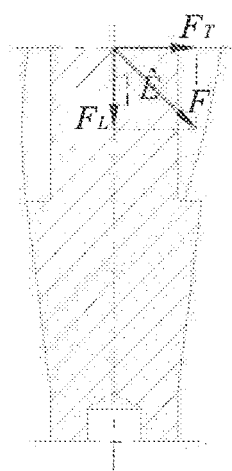
Fig. 5(a)    Fig. 5(b)
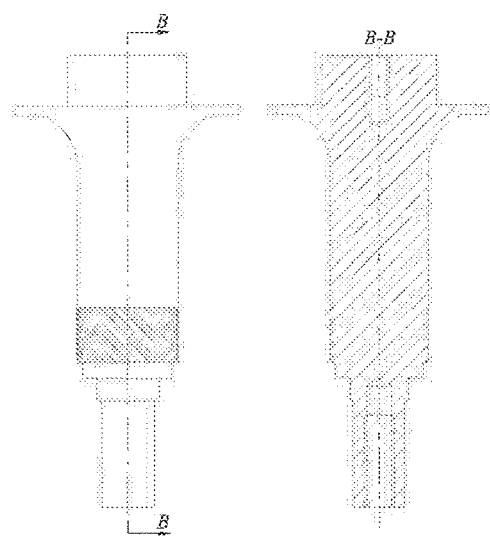
Fig. 6(a)    Fig. 6(b)

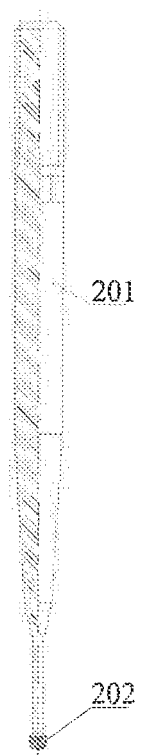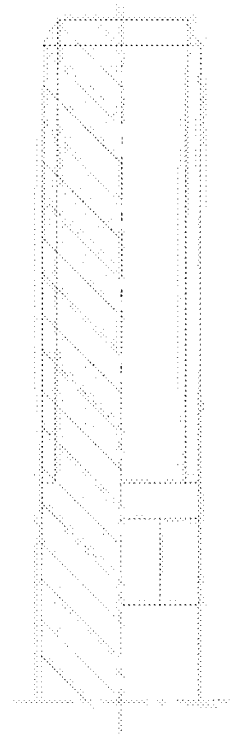
Fig. 7 Fig. 8
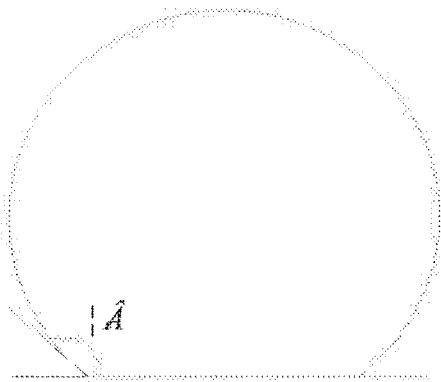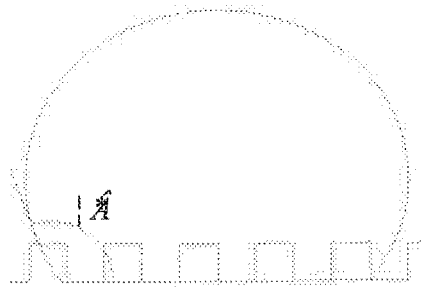
Fig. 9 Fig. 10
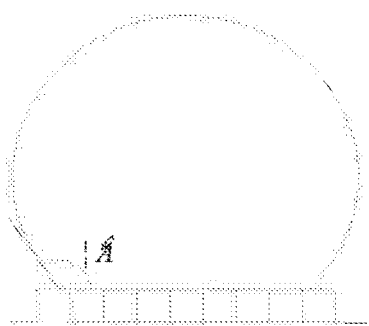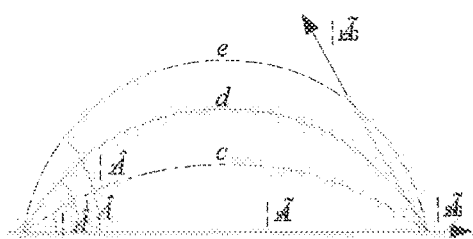
Fig. 11 Fig. 12

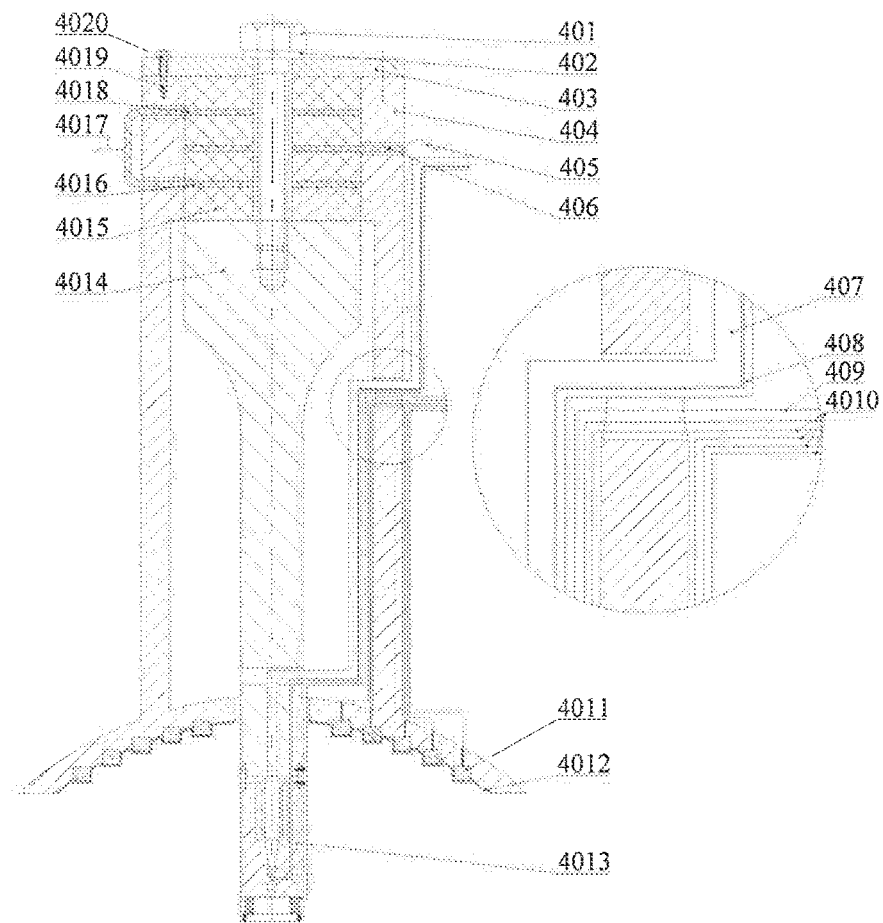
Fig. 18
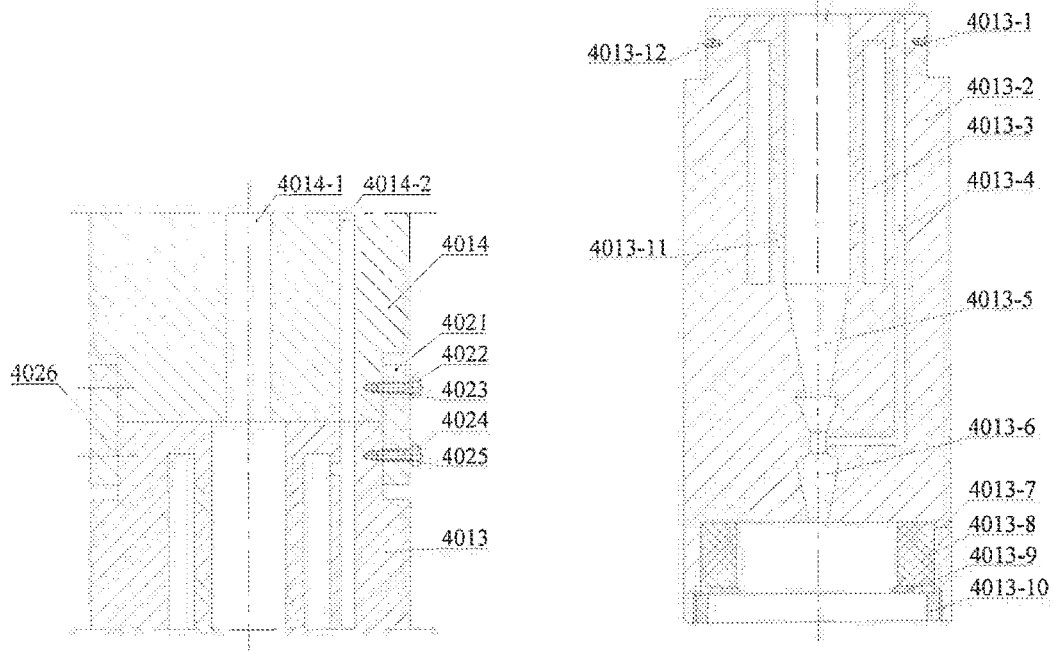
Fig. 19                    Fig. 20

Transducer

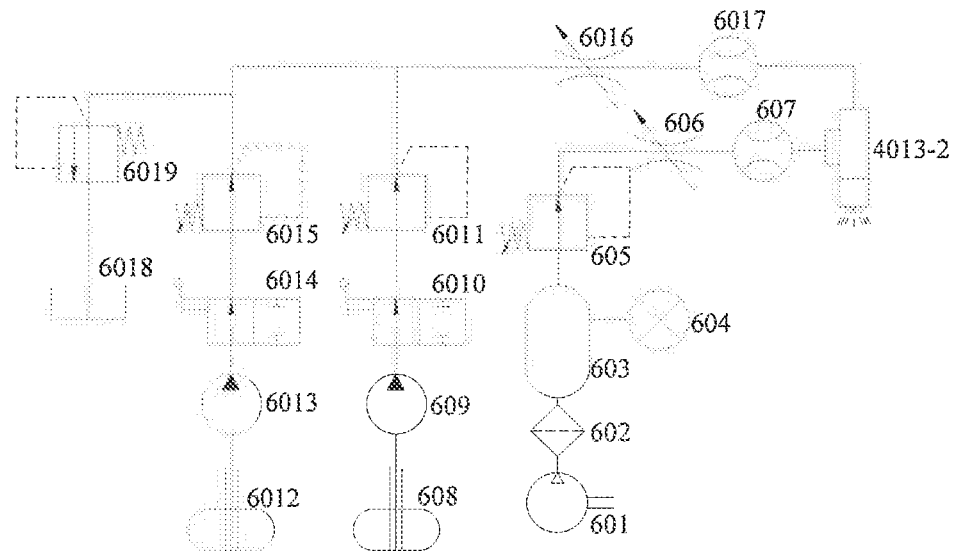
Fig. 24
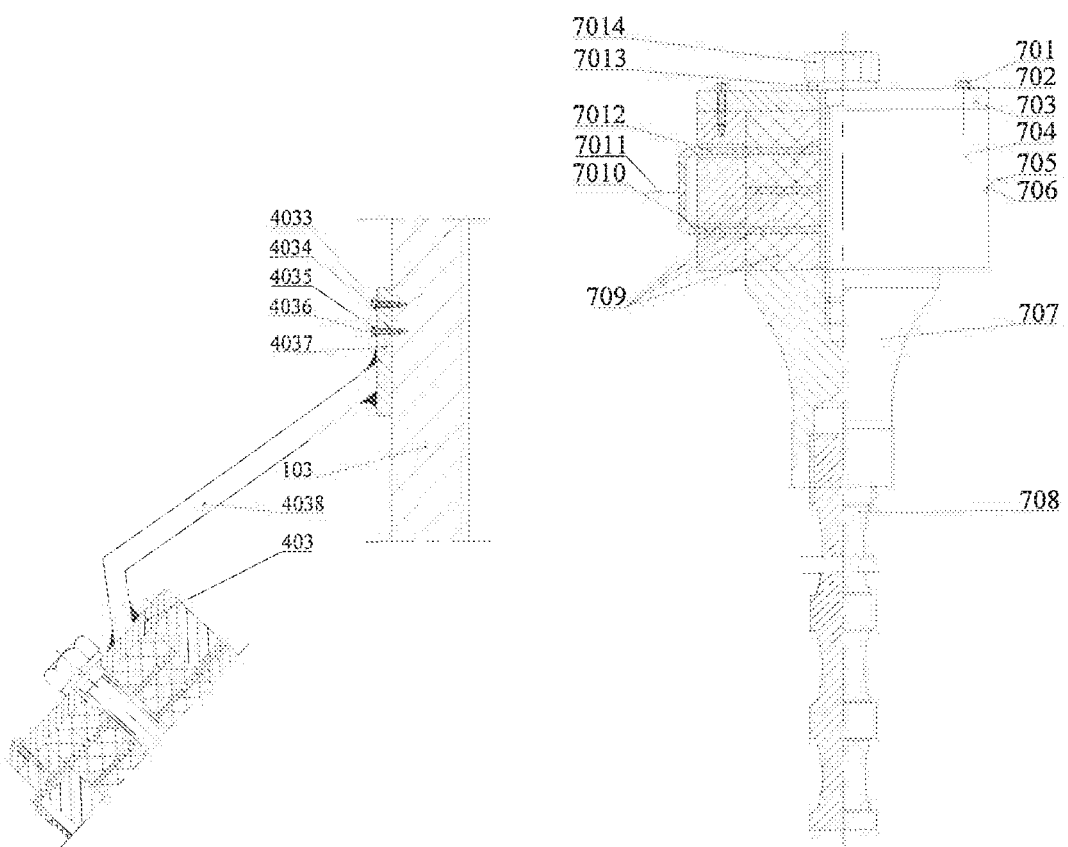
Fig. 25
Fig. 26

NEUROSURGICAL ULTRASONIC FOCUSING ASSISTED THREE-STAGE ATOMIZATION COOLING AND POSTOPERATIVE WOUND FILM FORMING DEVICE

FIELD OF THE INVENTION

The present invention relates to a neurosurgical skull grinding, intraoperative cooling and postoperative wound film forming flexible integrated device, in particular to a neurosurgical ultrasonic focusing assisted three-stage atomization cooling and postoperative wound film forming device.

BACKGROUND OF THE INVENTION

Bone grinding is one of common and basic surgical operations in skull base tumor removal surgery. In clinical practice, surgeons often use high-speed micro grinding wheels to remove bone pathology. However, the high-speed grinding produces a large amount of heat, which results in osteonecrosis and thermal damage to surrounding tissues and also has certain influence on the coagulation function of tissues. Saline drip cooling is often used in clinic, and part of the grinding heat is taken away by natural convection. The grinding thermal damage receives clinically recognized concern because the temperature cannot be determined during the grinding process and the degree of thermal damage cannot be controlled. Kondo et al. pointed out that in the cast saline cooling mode, the maximum critical temperature of thermal damage is 43° C., and when the temperature is more than 43° C., the optic nerve will be damaged, leading to blindness in severe cases. In term of bone grinding, facial paralysis and femoral head necrosis are also common problems in orthopedic surgery. Therefore, in the bone grinding surgery, the temperature control is directly related to the success or failure of the surgery.

By search, D. J. Filicicchia et al. from USA Illinois Spraying Systems Company invented an ultrasonic atomizing nozzle with a conical spray feature (patent number: ZL 200880125586.7), in which compressed air is applied to a nozzle assembly, and guided to an atomizing surface through ports, compartments and channels communicating each other. To obtain conical spray, the ports, compartments and channels guide the compressed air to rotate around an atomizing rod. Atomized droplets are entrained in the air as the rotating compressed air leaves the nozzle assembly through the adjacent atomizing surface. The rotating compressed air pushes the droplets forward, and the droplets move circumferentially outward in the form of conical spray.

By retrieval, Xiang Dong et al. from Tsinghua University invented a combined ultrasonic atomizing device (patent number: ZL 201010122821.4), in which the axis of a first-stage low-frequency ultrasonic atomizing nozzle and the front-end atomizing surface of a second-stage high-frequency ultrasonic atomizing nozzle array are configured at certain angle, and on the basis that a good liquid film is formed on the atomizing surface of the second-stage high-frequency ultrasonic atomizing nozzle array, sufficient amplitude is provided to cause the liquid to break into fine mist droplets under the action of surface waves, thereby enlarging the adaptive range of liquid atomization.

By search, Xiang Dong et al. from Tsinghua University invented a phase-controlled ultrasonic atomizing nozzle (patent number: ZL 201010122838.X), in which array elements are distributed in a group uniformly-spaced annular array manner, a support inlaid with the array elements is sandwiched between a front cover and a rear cover, the tip of a horn is a liquid atomizing surface, and the liquid to be atomized arrives at the surface through a central channel. By adopting the phase-controlled ultrasonic transducer array scheme, the size of a piezoelectric sheet of a single array element is reduced, a higher ultrasonic atomizing frequency can be provided, and based on the same horn, the amplitude of the atomizing surface can meet the atomization requirement of high-viscosity liquid.

By search, Li Hua et al. from Suzhou University of Science and Technology invented an ultrasonic focusing vapor mist cooler (patent number: ZL 201010221499.0), including a rear cover plate, a piezoelectric ceramic sheet, an electrode sheet, a horn, a focusing disc, a vibration transfer rod and a vapor mist cover, wherein the rear cover plate, the piezoelectric ceramic sheet and the electrode sheet are clamped by threads at the front end of bolts and the horn, the focusing disc is clamped between the vibration transfer rod and the horn by a dowel screw, the vapor mist cover is adhered to the focusing disc with an adhesive, the vibrator portion is of a sandwiched transducer structure, and the cooler has the advantages of large power capacity and strong vapor mist focusing capability, can furthest reduce the consumption of a coolant while ensuring efficient cooling, and thus achieves environment-friendly cooling.

By search, Mao Cong et al. from Changsha University of Science and Technology invented a lubricating and cooling method and device for a cutting process (patent number: ZL 201010551978.9), adding nano-particles with particle size of 20-40 nm at a volume ratio of 1-5% into vegetable oil or deionized water, adding a dispersant with a volume ratio of 0.05-0.15% and performing ultrasonic vibration at a frequency of 10-40 kHz to obtain a uniform oil-based or water-based nano-particle suspension with good dispersibility, sufficiently atomizing the nano-particle suspension into mist particles having a micron-scale diameter under the action of compressed air of 0.3-1 MPa, and ejecting the high-pressure mist particles by a nozzle to break through a cutter and an air barrier layer on the surface of a workpiece and reach a cutting zone so as to lubricate and cool the cutting zone.

By search, Li Hua et al. from Suzhou University of Science and Technology invented a split type ultrasonic focusing vapor mist cooling device (patent number: ZL 201310029236.3), in which transducers of an ultrasonic atomizer and an ultrasonic focuser are designed independently. The inherent frequencies of the ultrasonic atomizer and the ultrasonic focuser do not need to be the same. Compared with an integrated ultrasonic focusing vapor mist cooler, the split type ultrasonic focusing vapor mist cooling device is easy to manufacture, the relative positions of the ultrasonic vibration focuser and the ultrasonic vibration atomizer are easy to adjust, the ultrasonic vibration atomizer and the ultrasonic vibration focuser have higher power, the effects of ultrasonic atomization and ultrasonic focusing are better, and the late maintenance is convenient.

By search, Li Tao et al. from Qianteng (Nanjing) Environmental Protection Technology Co., Ltd. invented a natural focusing ultrasonic atomizing nozzle (patent number: ZL 201410648984.4), in which a liquid nozzle is fixedly arranged below a housing through a shock-absorbing support mechanism, a liquid outlet concentrically surrounds the end face of an atomizing head, and the nozzle can effectively solve the problems of the existing natural diverging atomizing nozzle, such as large size, ineffective liquid splash in the center hole, large relative air consumption, small maximum liquid flow rate and short spray distance.

By search, Wang Xiaoying et al. from Jiangsu University invented an electrostatic atomizing nozzle (patent number: ZL 201510161434.4), in which swivel ribs form a ribbed flow channel. When the swivel rotates, liquid enters the electrostatic atomizing nozzle in the circumferential direction, the liquid has a large axial velocity at the outlet of the ribbed flow channel, and the liquid mist at the outlet of the nozzle is tapered. The rotating seal realizes reliable axial seal, and needle electrodes are arranged reasonably to ensure the dryness of the electrodes and improve the charging efficiency and the electrical safety. The nozzle has the advantages of low energy consumption, less blockage and good charging effect, and can realize remote axial transport of rotary atomization.

By search, Li Haiying et al. from North China University of Science and Technology disclosed a double-medium atomizing nozzle for ultrasonic assisted atomization (application number: 201510630442.9), in which a piezoelectric ultrasonic transducer generates ultrasonic waves to produce a cavitation effect on water in a liquid chamber, at the same time, the oscillation of the ultrasonic waves also prevents impurities in the water from accumulating in the liquid chamber, thereby preventing the impurities in the water from accumulating on the inner wall of the nozzle and avoiding the phenomenon of nozzle blockage. The ultrasonic waves cause cavitation of the water in the liquid chamber to assist atomization, the cavitated water is ejected from a first spout, and the high-pressure steam is ejected from a second spout to impact a liquid film so as to break the liquid film.

By search, Song Zhiming from Dongguan Changyuan Spraying Technology Co., Ltd. designed a split type ultrasonic nozzle (patent number: ZL 201520738520.2), in which a core axially communicating with the nozzle body is arranged inside the nozzle body, a connecting pipe is arranged at the inlet end of the nozzle body, and a liquid flow channel is formed among the outer wall of the core, the outer wall of the connecting pipe and the inner wall of the nozzle body. An ultrasonic vibrating head is arranged outside the outlet end of the nozzle body, and multiple atomization is formed by combining the nozzle with the ultrasonic vibrating head.

By search, Wang Weiqiang et al. from Ningbo University designed a three-stage atomizing ultrasonic nozzle assembly (patent number: ZL 201520881683.6), in which a piezoelectric ceramic transducer is fixedly connected with the large end of a tapered horn, the small end of the tapered horn is fixedly connected with an atomizing nozzle, flow channels for introducing liquid are arranged in the piezoelectric ceramic transducer and the tapered horn, a plurality of atomizing holes distributed uniformly in the circumferential direction are arranged in the atomizing nozzle, the atomizing holes communicate with the flow channels, an atomizing disc is fixedly arranged at the small end of the tapered horn, and three-stage atomization of the liquid can be realized.

By search, Gao Jianmin et al. from Jiangsu University disclosed a low-frequency electrostatic ultrasonic atomizing nozzle (application number: 201610198692.4), in which a liquid inlet channel is arranged in the axial center of a horn of the nozzle, an air inlet channel is arranged at a position deviating from the axial center, a concave spherical surface is machined at the top of the horn of the nozzle, and a suspended ball is arranged on the concave spherical surface. The suspended ball is rotated at a high speed using compressed air moving axially eccentrically, the suspended ball generates an electric field by energizing the electrode, the droplets generated by low-frequency ultrasonic atomization are atomized again by static electricity, carrying electrostatic charges, and the charged droplets are ejected from the nozzle. Therefore, the nozzle breaks through the bottleneck that the low-frequency ultrasonic atomizing nozzle is difficult in generating superfine droplets, and enables the droplets to carry electrostatic charges so as to increase the adhesion thereof.

By search, Gao Jianmin et al. from Jiangsu University disclosed a two-phase flow ultrasonic atomizing device (application number: 201610334607.2), in which the liquid to be atomized is ejected by an air atomizing nozzle for the first atomization, and the ejected high-speed droplets impact on a high-frequency vibrating ultrasonic transducer and are broken into finer droplets for the second atomization.

By search, the existing pneumatic atomizing nozzles or electrostatic atomizing or ultrasonic atomizing nozzles all implement atomization using a single mechanism or a combination of two mechanisms, so that the atomizing effect of droplets cannot achieve the desired effect; and the droplets ejected from the nozzle body cannot be effectively and controllably injected into a grinding zone, and part of the droplets will be emitted into the surrounding environment, thereby reducing the convective heat transfer in the grinding zone. At present, there is no device or method that can achieve effective and controllable injection of droplets into a grinding tool/bone wedge constraint space while achieving superfine atomization of the droplets.

The electrospun fiber is soft, light and thin, and is full of nano-pores. As a wound dressing, it can fully bridge the wound. On the one hand, it reduces the stimulus of the external environment to the wound, protects the body fluid of the wound from evaporating too fast, and ensures that the wound can be exposed to the external fresh oxygen to facilitate the repair and growth of cells; and on the other hand, the electrospun nanofiber can filter most of bacteria and dust in the air to prevent the wound from being infected.

By search, Qin Xiaohong et al. from Donghua University invented an ultrasonic oscillating electrospinning nozzle and a method thereof (patent number: ZL 201110152579.X), in which a spinning solution or melt is added to a spinneret through an automatic infusion device, a controller and a high voltage are started, and the spinning solution or melt forms a Taylor cone under the action of ultrasonic oscillation and is jet up. The device overcomes the surface tension of the spinning solution or melt, forms multiple jets, increases the yield of electrospinning, and improves the spinning stability of the nozzle.

By search, Kong Qingshan et al. from Qingdao Institute of Bioenergy and Process, Chinese Academy of Sciences designed an ultrasonic-assisted electrospinning nanofiber preparation device (patent number: ZL 201220603914.3), in which an ultrasonic generator and an electrospinning preparation technology are combined, thereby exerting the characteristic that the polymer solution forms micro-droplets under the action of ultrasonic waves, overcoming the surface tension of the solution and the gravity of the droplets, easily forming a jet flow under the action of a high-voltage electric field and then forming nano-fibers, and improving the efficiency of preparing nanofibers by electrospinning.

By search, Chen Ming et al. from Yangzhou University invented a preparation method of porous electrospun nanofibers (patent number: ZL 201310600984.2), dissolving a polymer into an organic solvent, adding inorganic nanoparticles, performing ultrasonic dispersion to obtain an electrospinning solution, then spinning with the electrospinning solution on an electrospinning machine to obtain composite nanofibers of the nanoparticles and the polymer, finally, soaking the composite nanofibers of the nanoparticles and the polymer into a pore forming liquid to remove the nanoparticles and drying the composite nanofibers to obtain porous electrospun nanofibers. The obtained porous nanofibers have larger specific surface area and active sites than ordinary electrospun fibers, and can improve the load and the adsorption capacity.

By search, Yang Min et al. from Qingdao University of Technology invented a bone surgery grinding experimental device for cooling and electrostatic atomization film formation (Patent No.: ZL 201510604889.9), in which a grinding head is mounted at the lower end of an electric spindle, a grinding cooling device is arranged inside a grinding head handle or around the grinding head, an electrostatic atomization film forming device is arranged around the grinding head, and the grinding experimental device is suitable for reducing the temperature of a grinding zone in drip cooling, flood cooling, mist cooling, nanofluid mist cooling, phase change heat exchange type grinding heads, hydrophilic grinding heads, electrostatic atomizing inner cooling grinding tools, etc.

By search, Fang Feiyu et al. from Guangdong University of Technology disclosed an ultrasonic porous bubble electrospinning device (application number: 201510778831.6), in which a high-voltage electrostatic generator is connected with a receiving device and a reservoir respectively, an electric field required to generate a jet is formed between a rotating center of a support arm and the reservoir, and an exhaust device is arranged above a bowl-shaped rotating surface to form airflow passing through the bowl-shaped rotating surface from the bottom to the top. The spinning efficiency per unit time is greatly increased, and the problem of difficult collection of a three-dimensional fiber bracket is also solved.

By search, the conventional electrospinning devices all have the characteristic of large size, which is not conducive to the flexible and convenient use of a surgeon in a narrow space. Only the electric field force of droplets overcomes the surface tension so that the droplets form a jet, and the formed fibers are thicker. There is no spinning device or method that enables an operator to operate flexibly while superfine fibers are formed, and even there is no device that can effectively inject a coolant after superfine atomization into a grinding zone for cooling, and can realize film forming coating of the superfine spun fibers on a surgical wound.

SUMMARY OF THE INVENTION

In order to overcome the deficiencies of the prior art, the present invention provides a neurosurgical ultrasonic focusing assisted three-stage atomization cooling and postoperative wound film forming device, which is small in size and facilitates flexible and convenient operation of a surgeon in a narrow space; superfine droplets are obtained after pneumatic-ultrasonic-electrostatic three-stage atomization of a medical nanofluid coolant in the surgery, and the nanofluid droplets are injected into a grinding tool/bone wedge-shaped constraint space by ultrasonic focusing to effectively cool and lubricate a grinding zone; and at the end of the surgery, the spinning system applied to wound dressing is sprayed onto a postoperative wound surface in the form of spinning fibers after three-stage atomization to achieve atomized film forming protection on the ground wound surface.

A specific scheme of a neurosurgical ultrasonic focusing assisted three-stage atomization cooling and postoperative wound film forming device is as follows:

A neurosurgical ultrasonic focusing assisted three-stage atomization cooling and postoperative wound film forming device, including:

a transducer housing, wherein a horn II is arranged in the transducer housing, at least two layers of piezoelectric ceramic sheets II are arranged at the top of the horn II, an electrode sheet connected with an ultrasonic generator is arranged between two adjacent layers of piezoelectric ceramic sheets II, the bottom of the transducer housing is of a hemispherical structure, a plurality of piezoelectric elements connected with the ultrasonic generator are arranged inside the hemispherical structure, a copper mesh common electrode is arranged on the surface of the piezoelectric elements, the bottom of the horn II protrudes the hemispherical structure of the transducer, high-frequency electric oscillation signals are converted into an axial high-frequency vibration, and the horn II is closely connected with the piezoelectric ceramic sheets II to amplify the amplitude; and a nozzle, arranged at the bottom of the horn II, wherein the nozzle is connected with a medical nanofluid (a mixture of normal saline and solid nanoparticles) storage cup, compressed gas can be introduced into the nozzle, an electrode is arranged inside the nozzle, and medical nanofluid is flushed into a grinding zone in the form of droplets for effective cooling and lubrication after pneumatic-ultrasonic-electrostatic atomization, and a postoperative wound can be coated effectively.

According to the device, the nanofluid is ejected by the nozzle, axial high-frequency vibration at the nozzle is realized under the action of an ultrasonic amplitude rod, the nanofluid subjected to pneumatic, ultrasonic vibration and static electricity enters the grinding zone for cooling, and the droplets can also protect the wound surface after cooling.

Further, a liquid inlet channel and an air inlet channel are arranged inside the horn II, the liquid inlet channel communicates with a nanofluid inlet of the nozzle, and the air inlet channel communicates with a compressed gas inlet of the nozzle;

or, the electrode is connected with an external high-voltage electrostatic generator to charge the nanofluid droplets.

Further, a nanofluid channel and a compressed gas channel are arranged in the nozzle, an internal compressed gas channel communicating with the nanofluid channel is also arranged in the nozzle, an acceleration chamber is arranged at the bottom of the nanofluid channel, the compressed gas channel communicates with the acceleration chamber, and the internal compressed gas channel enters the nanofluid channel through a swirling compressed gas channel;

Alternatively, the transducer housing is provided with an opening, a nanofluid tube and a compressed gas tube respectively penetrate through the opening and communicate with the liquid inlet channel and the air inlet channel, and then enter the nanofluid channel and the compressed gas channel through the nanofluid inlet and the compressed gas inlet respectively.

Further, the acceleration chamber includes two communicating reducing sections, both of the first reducing section and the second reducing section are in an inverted circular truncated cone shape, the second reducing section is connected with a third section through a cylinder section, the third section is a vortex chamber, the vortex chamber includes an expanding section and a reducing section, compressed gas enters the nanofluid channel at a set speed through the swirling compressed gas channel and then is mixed with the nanofluid to form a three-phase flow of high-pressure gas, normal saline and solid nanoparticles, the three-phase flow is accelerated in the first and second sections of the acceleration chamber, the accelerated three-phase flow enters the vortex chamber to form a vortex with compressed air therein, and the three-phase flow is further mixed and then ejected through the outlet of the nozzle to form droplets. The ejected droplets pass through a drift region of corona discharge of needle electrodes, collide with drifting electrons and are charged, and the charged droplets are controlled to be sprayed to the surface of an acting zone under the action of electric field force, aerodynamic force and gravity.

Further, the piezoelectric elements are arranged on the circumference of a plurality of concentric circles, thus forming an adjustable focus and ensuring efficient injection of the nanofluid droplets into the grinding zone, wherein the piezoelectric elements are wafer piezoelectric elements.

In order to overcome the deficiencies of the prior art, the present invention further provides a low-damage and controllable biotic bone grinding device, including: a neurosurgical ultrasonic focusing assisted three-stage atomization cooling and postoperative wound film forming device;

a spindle, arranged in an electric spindle housing, wherein a rotor winding is arranged on the circumference of the outer surface of the spindle, a stator winding corresponding to the rotor winding is arranged in the electric spindle housing, and the stator winding can be energized to drive the spindle to rotate; and a water-catching grinding tool for grinding a biotic bone, wherein the spindle is connected with the water-catching grinding tool through an ultrasonic vibration mechanism, the water-catching grinding tool achieves longitudinal-torsional and rotary motions under the drive of the spindle and the ultrasonic vibration mechanism, and the surface of the water-catching grinding tool is provided with micro-bulges.

The device is small in size, and a surgeon can operate flexibly. The spindle can realize rotation and longitudinal vibration at the same time, which is beneficial to the timely discharge of bone chips and achieves high grinding efficiency. The water-catching grinding head with micro-bulges has super-hydrophilic and water-catching properties, thereby enhancing the convective heat exchange of the grinding zone and reducing the bone grinding temperature.

In addition, in order to further ensure the integration of the device, the device further includes an endoscope, an endoscope body is fixed to the electric spindle housing, and an endoscope lens is arranged on one side of the water-catching grinding tool.

Further, the ultrasonic vibration mechanism includes four layers of piezoelectric ceramic sheets I, an electrode sheet connected with the ultrasonic generator is arranged between two adjacent layers of piezoelectric ceramic sheets I, and the bottom piezoelectric ceramic sheet I is connected with the top of the water-catching grinding tool through a horn i.

The top of the spindle and the bottom of the horn I are respectively fixed to the electric spindle housing by a tapered roller bearing.

The spindle is connected with a connecting cylinder through a coupling, the piezoelectric ceramic sheets I are arranged at the bottom of the connecting cylinder, a sleeve is arranged inside the electric spindle housing, and electric brushes connected with respective electrode sheets are arranged in the sleeve.

Further, the top of the spindle and the bottom of the horn I are respectively fixed to the electric spindle housing by a tapered roller bearing, and the surface of the horn I is provided with rectangular spiral grooves to realize longitudinal torsional resonance of the spindle.

Further, the water-catching grinding tool includes a grinding tool handle, a spherical grinding head base is arranged at the bottom of the grinding tool handle, the spherical grinding head base includes a partial sphere, a plurality of octagonal cylinders are arranged on the surface of the partial sphere, the octagonal cylinders are connected in series up and down, a plurality of square cylindrical micro-bulges are formed on the surface of the octagonal cylinders, and a nano separator film is adhered among the micro-bulges on the surface of the octagonal cylinders.

Further, the spindle is connected with a connecting cylinder through a coupling, the piezoelectric ceramic sheets I are arranged at the bottom of the connecting cylinder, the longitudinal cross section of the connecting cylinder is H-shaped, a sleeve is arranged inside the electric spindle housing, electric brushes connected or contacted respectively with each electrode sheet are arranged in the sleeve, a power interface II is arranged on the electric spindle housing, a power line is connected with the brushes through one end of the power interface II, and the other end is connected with the ultrasonic generator.

Further, an end cover is respectively arranged at the top and the bottom of the electric spindle housing, the water-catching grinding tool penetrates through the bottom end cover, the end covers are fixed to the electric spindle housing by fasteners and sealing gaskets in order to facilitate the maintenance of the device, and bulges are provided on the inner sides of the end covers to achieve effective engagement with the electric spindle housing.

Further, an ultrasonic vibration bar is arranged in the fluid storage cup in order to ensure the coating effect, the ultrasonic vibration bar is connected with the ultrasonic generator, ultrasonic oscillation is performed on the medical nanofluid in the fluid storage cup through the ultrasonic vibration bar, and the obtained superfine fibers are sprayed onto the postoperative wound surface to form a fiber film for coating the postoperative wound to prevent wound infection, wherein a horn III is arranged at the top of the ultrasonic vibration bar, four layers of piezoelectric ceramic sheets III are arranged at the top of the horn III, an electrode sheet connected with the ultrasonic generator is arranged between two adjacent layers of piezoelectric ceramic sheets III, and a top cover II, the piezoelectric ceramic sheets III and the horn III are connected by screws.

Moreover, in order to ensure wiring, a fiber channel II is arranged inside the electric spindle housing, and a fiber channel I communicating with the fiber channel II is arranged inside the endoscope body.

Compared with the prior art, the present invention has the following advantages:

1) The device of the present invention can eject nanofluid, the nanofluid can form superfine droplets by pneumatic, ultrasonic vibration and electrostatic action to ensure the cooling effect on the wound, and the nanofluid is effectively injected into the grinding zone for heat exchange through the piezoelectric elements connected with the ultrasonic mechanism so as to reduce the bone grinding temperature.

2) Through the micro-bulges and the nano separator film, the water-catching grinding tool has super-hydrophilic and water-catching properties, thereby enhancing the convective heat exchange in the grinding zone and reducing the bone grinding temperature.

3) The spindle is an electric spindle and has a brush-type structure, so the overall structure is small, and the problems that the conventional hand-held surgical device is large in working space, high in operation difficulty and low in operation efficiency and may bring unnecessary additional damage to the patient are solved; the operation is convenient and flexible, and the problem that the surgeon is prone to fatigue during the operation is solved.

4) Ultrasonic vibration of fluid in the fluid storage cup can be realized through the ultrasonic vibration bar, thereby effectively reducing the viscosity of an electrospinning solution and a melt, expanding the electrospinning concentration range of the device, effectively reducing the diameters of fibers, reducing the structural defects of the fibers, improving the mechanical properties of the spinning fibers, and ensuring that the spinning system for wound dressing is sprayed onto the postoperative wound surface in the form of spinning fibers after three-stage atomization to achieve atomized film forming protection on the ground wound surface.

5) The nozzle is connected with the nanofluid and the compressed gas to realize pneumatic atomization on the medical nanofluid coolant, the electrodes can implement electrostatic treatment on the droplets, and the horns can cavitate the droplets, so that the medical nanofluid at the working surface forms superfine droplets after pneumatic-ultrasonic-electrostatic three-stage atomization; and the nanofluid droplets are injected into the grinding tool/bone wedge-shaped constraint space by ultrasonic focusing to effectively cool and lubricate the grinding zone.

6) The whole device is small in structure and high in integration, and is convenient for a surgeon to operate flexibly and conveniently in a narrow surgical space.

BRIEF DESCRIPTION OF THE DRAWINGS

The accompanying drawings constituting a part of the present application are used for further understanding the present application, and the schematic embodiments of the present application and the description thereof are used for interpreting the present application, rather than constituting improper limitation to the present application.

FIG. 1 is an assembly diagram of an electrostatic atomization ultrasonic assisted low-damage and controllable biotic bone grinding process and device;

FIG. 2 is a cross-sectional view of a longitudinal torsional resonant rotary ultrasonic electric spindle;

FIG. 3 is a schematic diagram of part of an ultrasonic mechanism;

FIG. 4 shows an exponential segment function of a horn;

FIGS. 5(*a*) and 5(*b*) are force analysis diagrams of a rectangular spiral groove horn;

FIGS. 6(*a*) and 6(*b*) show a triangular fence group through slot horn;

FIG. 7 shows a neurosurgical skull grinding water-catching grinding tool;

FIG. 8 is an enlarged view of the upper part of a grinding tool handle;

FIG. 9 shows a droplet Young's wetting model;

FIG. 10 shows a droplet Wenzel wetting model;

FIG. 11 shows a droplet Cassie wetting model;

FIG. 12 is a schematic diagram of a droplet pinning effect;

FIG. 13 shows a three-phase contact boundary of the Wenzel wetting model;

FIG. 14 shows a three-phase contact boundary of the Cassie wetting model;

FIG. 15 is a surface dimension diagram of square cylindrical bulge microstructures;

FIG. 16 is a grinding head base of the water-catching grinding tool and a cross-sectional view;

FIG. 17(*a*) is a cross-sectional view of the front view of the grinding head;

FIG. 17(*b*) is a cross-sectional view of the top view of the grinding head;

FIG. 18 is a cross-sectional view of a three-stage atomization focus adjustable ultrasonic focusing nozzle;

FIG. 19 is a connection diagram of a nozzle body and a horn;

FIG. 20 is a cross-sectional view of a pneumatic-electrostatic atomizing nozzle;

FIG. 21 is an assembly diagram of a spherical crown portion of a spherical crown transducer housing and a bottom view thereof;

FIG. 22 is a principle diagram of a focus adjustable transducer;

FIG. 23 is a principle diagram of electrospinning;

FIG. 24 is a diagram showing a fluid path and gas path system of a cooling and film forming mechanism;

FIG. 25 is a connection diagram of the cooling and film forming mechanism and an electric spindle;

FIG. 26 is a half cross-sectional view of an ultrasonic vibration bar;

FIG. 27 is an installation diagram of an endoscope in an electric spindle housing;

FIG. 28 is a cross-sectional view of the interior of the endoscope body.

In which, 1—longitudinal torsional resonant rotary electric spindle, 2—water-catching grinding tool, 3—endoscope, 4—cooling and film forming mechanism, 5—ultrasonic generator, 6—fluid storage cup, 7—ultrasonic vibration bar;

101—end cover I, 102—spacer I, 103—electric spindle housing, 104—spindle, 105—power interface I, 106—power line I, 107—stator winding, 108—rotor winding, 109—coupling, 1010—threaded hole I, 1011—connecting cylinder, 1012—short brush, 1013—power interface II, 1014—power line II, 1015—electrode sheet I, 1016—sleeve, 1017—horn I, 1018—conical roller bearing I, 1019—threaded hole II, 1020—threaded hole III, 1021—spacer II, 1022—end cover II, 1023—sealing ring, 1024—spring washer I, 1025—screw i, 1026—threaded hole IV, 1027—threaded hole V, 1028—piezoelectric ceramic sheet I, 1029—electrode sheet II, 1030—long brush, 1031—electrode sheet III, 1032—spring washer II, 1033—center screw I, 1034—conical roller bearing II, 1035—screw II, 1036—spring washer III;

201—grinding tool handle, 202—grinding head base; 202—1—partial sphere, 202—2—octagonal cylinder, 202—3—square cylindrical micro-bulge, 202—4—nano separator film; 301—screw II, 302—spring washer IV, 303—endoscope body, 304—screw IV, 305—spring washer V, 306—fibre channel, 307—fibre channel II, 308—cold light illumination source transmission fiber, 309—endoscope fiber, 3010—fluorescence excitation light transmission fiber, 3011—image transmission fiber;

401—center screw II, 402—spring washer VI, 403—top cover I, 404—spherical crown transducer housing, 405—electric excitation signal line I, 406—electrode sheet IV, 407—fluid inlet pipe, 408—air inlet pipe, 409—high voltage wire, 4010—electric excitation signal line II, 4011—plane wafer piezoelectric element, 4012—copper mesh common electrode, 4013—electrostatic atomizing nozzle, 4014—horn II, 4015—piezoelectric ceramic sheet II, 4016—electrode sheet V, 4017—electric excitation signal line III, 4018—electrode sheet VI, 4019—screw V, 4020—spring washer VII, 4021—connecting plate I, 4022—screw VI, 4023—spring washer VIII, 4024—screw VII, 4025—spring washer IX, 4026—connecting plate II, 4027—high-voltage electrostatic generator, 4028—injection pump, 4029—spinning medium, 4030—metal electrode, 4031—fiber jet, 4032—receiving plate; 4033—screw VIII, 4034—spring washer X, 4035—screw IX, 4036—spring washer XI, 4037—connecting plate III, 4038—connecting rod;

4013-1—threaded hole VI, 4013-2—nozzle body, 4013-3—internal compressed gas channel, 4013-4—compressed gas channel, 4013-5—three-phase flow acceleration chamber, 4013-6—vortex chamber, 4013-7—high voltage inlet hole, 4013-8—electrode tray, 4013-9—needle electrode, 4013-10—positioning threaded ring, 4013-11—swirling compressed gas channel, 4013-12—threaded hole VII, 4013-13—nanofluid inlet, 4013-14—compressed gas inlet; 4014-1—liquid inlet channel, 4014-2—air inlet channel;

601—air compressor, 602—filter, 603—gas tank, 604—pressure gauge, 605—pressure regulating valve I, 606—throttle valve I, 607—turbine flow meter I, 608—fluid storage cup I, 609—hydraulic pump I, 6010—reversing valve I, 6011—pressure regulating valve II, 6012—fluid storage cup II, 6013—hydraulic pump II, 6014—reversing valve II, 6015—pressure regulating valve III, 6016—throttle valve II, 6017—turbine flow meter II, 6018—recycling tank, 6019—overflow valve;

701—screw X, 702—spring washer XII, 703—top cover II, 704—transducer housing, 705—electric excitation signal line IV, 706—electrode sheet VII, 707—horn III, 708—vibration bar, 709—piezoelectric ceramic sheet III, 7010—electrode sheet VIII, 7011—electric excitation signal line V, 7012—electrode sheet IX, 7013—spring washer XIII, 7014—center screw III.

DETAILED DESCRIPTION OF THE EMBODIMENTS

It should be pointed out that the following detailed descriptions are all exemplary and aim to further illustrate the present application. Unless otherwise specified, all technical and scientific terms used in the descriptions have the same meanings generally understood by those of ordinary skill in the art of the present application.

It should be noted that the terms used herein are merely for describing specific embodiments, but are not intended to limit exemplary embodiments according to the present application. As used herein, unless otherwise explicitly pointed out by the context, the singular form is also intended to include the plural form. In addition, it should also be understood that when the terms "include" and/or "comprise" are used in the specification, they indicate features, steps, operations, devices, components and/or their combination.

As described in the background, the prior art has deficiencies. In order to solve the above technical problems, the present application proposes a neurosurgical ultrasonic focusing assisted three-stage atomization cooling and postoperative wound film forming device.

In a typical embodiment of the present application, FIG. 18 shows a neurosurgical ultrasonic focusing assisted three-stage atomization cooling and postoperative wound film forming device. In the device, a top cover I 403, piezoelectric ceramic sheets II 4015, an electrode sheet IV 406, an electrode sheet V 4016 and an electrode sheet VI 4018 are closely connected with a horn II 4014 through a center screw II 401 and a spring washer VI 402. A spherical crown transducer housing 404, the electrode sheet V 4016, the piezoelectric ceramic sheets II 4015, the electrode sheet VI 4018 and the electrode sheet IV 406 constitute a transducer. During operation, an ultrasonic generator 5 converts alternating current into high-frequency electric oscillation signals, the high-frequency electric oscillation signals are respectively transmitted to the electrode sheet IV 406, the electrode sheet V 4016 and the electrode sheet VI 4018 through an electric excitation signal line I 405 and an electric excitation signal line III 4017 and converted into an axial high-frequency vibration, and the horn II 4014 is closely connected with the piezoelectric ceramic sheets II 4015 to amplify the amplitude so as to implement ultrasonic cavitation on the nanofluid. The spherical crown transducer housing 404 is tightly connected with the top cover I 403 by screws V 4019 and spring washers VII 4020.

Figure 21:
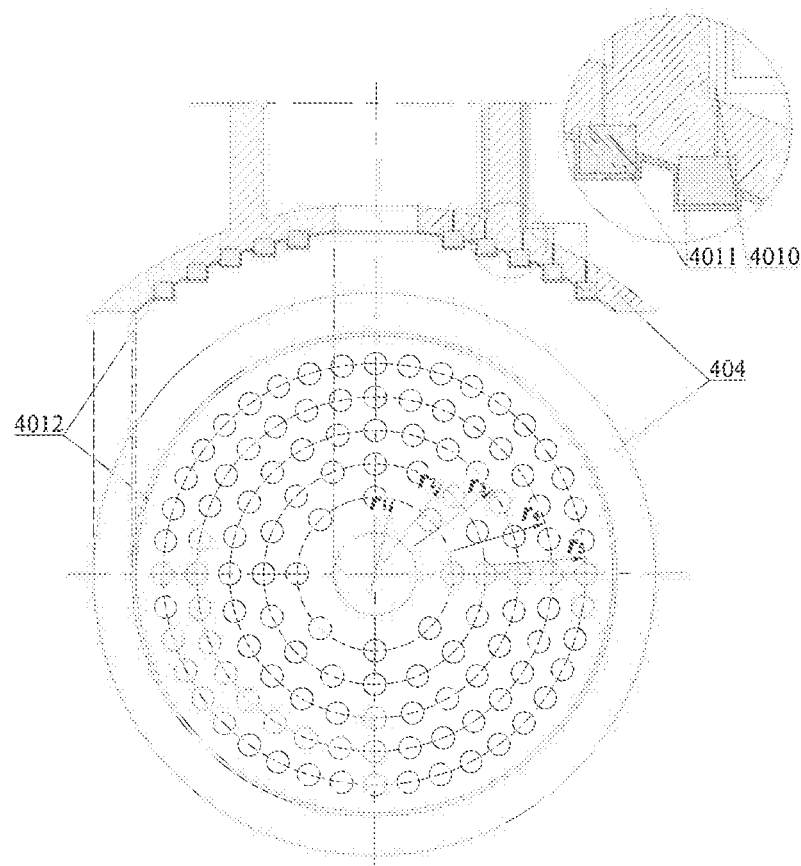
Figure 22:
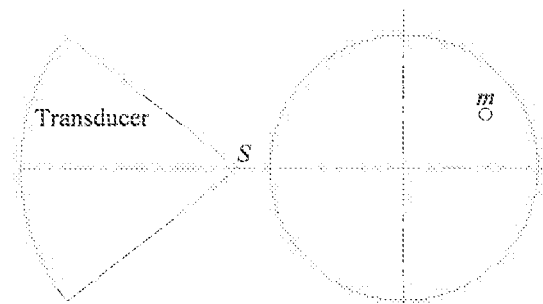
Figure 23:
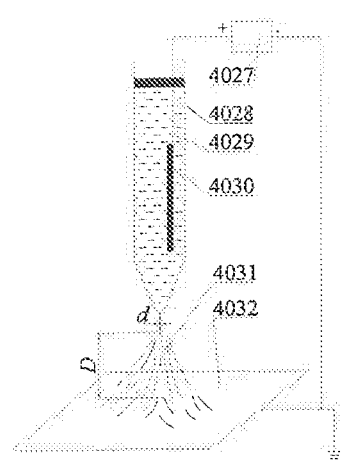

As shown in FIG. 19 and FIG. 20, a threaded hole VI 4013-1 and a threaded hole VII 4013-12 are machined at the upper end of the electrostatic atomizing nozzle 4013, and the electrostatic atomizing nozzle 4013 is fixed at the lower end of the horn II 4014 by a connecting plate I 4021 and a connecting plate II 4026 through screws VI 4022, screws VII 4024, spring washers VIII 4023 and spring washers IX 4025. FIG. 21 shows a cross-sectional view of the electrostatic atomizing nozzle. The nozzle body is complicated in structure, difficult to manufacture and is required to have certain insulating property, so the nozzle body is manufactured using a ceramic material through a rapid molding process. Compressed gas entering from a compressed gas inlet 4013-14 passes through an internal compressed gas channel 4013-3 and a swirling compressed gas channel 4013-11 to enter a mixing chamber at a set tangential velocity, and is mixed with a nanofluid entering from a nanofluid inlet 4013-13 to form a three-phase flow of high pressure gas, normal saline and solid nanoparticles. The three-phase flow is accelerated by an acceleration chamber 4013-5, then enters a vortex chamber 4013-6 and forms vortex therein together with compressed air entering through a vortex chamber compressed gas channel 4013-4, and the three-phase flow is further mixed and then ejected through an outlet of a nozzle body 4013-2 to form droplets. The ejected droplets pass through a drift region of corona discharge of needle electrodes 4013-9, collide with drifting electrons and are charged, and the charged droplets are controlled to be sprayed to the surface of a workpiece under the action of electric field force, pneumatic pressure and gravity.

The electrode tray 4013-8 is made of an insulating material, and a high voltage inlet hole 4013-7 is formed in the electrode tray 4013-8. As shown in FIG. 20, eight electrode slots are circumferentially arrayed in the electrode tray 4013-8, the needle electrodes 4013-9 (in interference fit with the electrode slots, clamped by the elastic deformation of the insulating material) are mounted in the electrode slots, and the respective needle electrodes 4013-9 are connected in series by a high voltage wire 409 and led out via a leading-out through hole of the high voltage wire tray. A positioning threaded ring 4013-10 mainly plays a role in positioning the electrode tray 4013-8.

Electrostatic atomization mechanism: When there is a high relative velocity between the droplets and the surrounding gas, the splitting of the droplets is controlled by pneumatic pressure, surface tension and viscous force. For liquid with low viscosity, the breakage of the droplets is mainly determined by the pneumatic pressure and the surface tension. The pneumatic pressure borne by large droplets is $0.5\rho_g \Delta V^2$, wherein $\rho_g$ is the density of gas and $\Delta V$ is the gas-liquid relative velocity. However, the cohesive force generated by the surface tension will hinder the deformation and breakage of the droplets, and the cohesive force can be expressed as $4\sigma/D$, wherein a is the inherent surface tension of liquid, and D is the initial diameter of droplets. When the diameter of the droplets is reduced, the cohesive force is increased. When the cohesive force and the tensile stress caused by the pneumatic pressure achieve a balance, the droplets remain stable, and if the two cannot cancel each other, the droplets will be deformed or even broken. According to the principle that the tensile stress generated by the pneumatic pressure acting on the droplets and the cohesive force generated by the surface tension are balanced, a dimensionless number can be obtained:

$$We = \frac{\rho_g \Delta V^2 D}{\sigma} = 8 \tag{1}$$

It can be seen that when We is more than 8, the droplets are unbalanced in stress and deformed. In addition, a maximum steady-state droplet diameter corresponding to $\Delta V$ can be solved according to (1):

$$D_{max} = \frac{8\sigma}{\Delta V^2 \rho_g} \tag{2}$$

Under the action of Coulomb repulsion, the surface tension of the charged droplets becomes weak, and the weak surface tension value is:

$$\sigma' = \sigma - \frac{q^2}{64\pi^2 \varepsilon r^3} \tag{3}$$

In which: r is the radius of a droplet; q is the charged quantity of the droplet; and ε is a dielectric constant of the surrounding air. It can be seen from equation (3) that when the charge quantity q increases, the surface tension declines, so the charged surfaces of the droplets contribute to atomization. At this moment, We of the charged droplets can be expressed as:

$$We = \frac{\rho_g \Delta V^2 D}{\sigma - \frac{q^2}{64\pi^2 \varepsilon r^3}} = \frac{128\pi^2 \varepsilon R^4 \rho_g \Delta V^2}{64\pi^2 \varepsilon R^3 \sigma - q^2} \tag{4}$$

It can be seen from equation (4) that the breakage of the charged droplets in the high-speed gas flow is closely related to a gas-liquid relative velocity, gas-liquid physical parameters and a charging field. In addition, if the droplets reach a steady state in the gas flow, after the droplets are charged with static electricity, the number We increases, the surface tension of the liquid decreases and fails to resist the pneumatic pressure, and the droplets will be further deformed and broken, so the diameters of the droplets charged with static electricity are smaller under the same gas-liquid parameters, and the purpose of thinning the droplets is achieved; at the same time, the same charge on the surfaces of the droplets can ensure more uniform distribution of the droplets. Therefore, the device can realize pneumatic and ultrasonic atomization and then electrostatic atomization, totally goes through three stages of atomization, finally obtaining superfine droplets distributed uniformly.

As shown in FIGS. 21, 8, 16, 24, 32 and 40 circular holes are respectively distributed on concentric circles $r_1$, $r_2$, $r_3$, $r_4$ and $r_5$ around the center, plane wafer piezoelectric elements

4011 are nested in the circular holes, and all of the plane wafer piezoelectric elements 4011 have the same diameter and thickness. A copper mesh common electrode 4012 covers the lower ends of the plane wafer piezoelectric elements 4011 and is adhered to all the plane wafer piezoelectric elements 4011 with an adhesive, and the bottom surface of the spherical crown portion is pressed by a pressure table, so that the adhered ends of the copper mesh common electrode 4012 and the plane wafer piezoelectric elements 4011 are flattened. The upper surfaces of all the plane wafer piezoelectric elements 4011 on the circles having the radii of $r_1$, $r_2$, $r_3$, $r_4$ and $r_5$ are connected into a circuit by electric excitation signal lines II 4010, and the circuit is separately excited by a power supply to form a branch.

The Westervelt sound wave propagation equation is:

$$\nabla^2 p - \frac{1}{c_0^2}\frac{\partial^2 p}{\partial t^2} + \frac{\delta}{c_0^4}\frac{\partial^3 p}{\partial t^3} + \frac{\beta}{\rho_0 c_0^4}\frac{\partial^2 p^2}{\partial t^2} = 0 \tag{5}$$

Wherein: $\nabla$ is a Laplacian operator; p is sound pressure; $c_0$ and $\rho_0$ are respectively sound velocity and density of a medium; $\beta=1+B/(2A)$ is a nonlinear coefficient of sound waves, and B/A is a nonlinear coefficient of a fluid medium; $\delta=2c_0^3\alpha/\omega^2$ is a sound wave diffusion coefficient; $\alpha$ is an absorption coefficient; $\omega=2\pi f$ is an angular frequency; and f is frequency.

The central difference is performed on equation (5) by adopting a time domain finite difference method. The difference equation is:

$$p^{n+1(}i,\ j,\ k) = \frac{1}{H}\left[c_0^2(dt)^2\nabla^2 p + H_1 p^n(i,\ j,\ k) - H_2 p^{n-1}(i,\ j,\ k)\right] + \frac{H_3}{H}[34p^{n-2}(i,\ j,\ k) - 24p^{n-3}(i,\ j,\ k) + 8p^{n-4}(i,\ j,\ k) - p^{n-5}(i,\ j,\ k)] \tag{6}$$

Wherein, $$H = 1\frac{4\beta}{\rho c_0^2}p^n(i,\ j,\ k) + \frac{2\beta}{\rho c_0^2}p^{n-1}(i,\ j,\ k),$$

$$H_1 = 2 + \frac{3\delta}{c_0^2 dt} - \frac{6\beta}{\rho c_0^2}p^n(i,\ j,\ k) + \frac{4\beta}{\rho c_0^2}p^{n-1}(i,\ j,\ k),$$

$$H_2 = 1 + \frac{23\delta}{c_0^2 dt},\ H_3 = \frac{\delta}{2c_0^2 dt};\ i,$$

j and k are coordinates in three coordinate axes x, y and z under a rectangular coordinate system; dx, dy and dz respectively represent spatial step sizes in the three coordinate axes x, y and z; dt is a time step; n is a calculation time.

As shown in FIG. 22, a sinusoidal point source $S_0(t)$ is set at a target focus S, and the numerical simulation is performed to obtain a sound pressure signal $S_{0m}(t)$ which is transmitted to the center point of the array element m of the phased array, and the signal is inverted according to a time series to obtain a signal $S_{0m}(T-t)$ corresponding to the array element m. The relative initial phase delay $\Delta t_m$ of the $S_{0m}(T-t)$ is calculated using least squares function fitting, and then the amplitude of the sinusoidal signal is modulated with the same input sound intensity. The excitation signal for the array element m is:

$$S_{0m}(t)=P_0 \sin(\omega(t+\Delta t_m)) \tag{7}$$

The phase of each array element is controlled by controlling the excitation signal for the array element, so that the sound beam of each array element reaching a certain point (set focus) of the space has the same phase. Continuous and dynamic adjustment on the size and position of the focus is finally realized by controlling the shape of sound beams, the distribution of sound pressure and the angles of the sound beams.

FIG. 18 is a cross-sectional view of the three-stage atomization focus adjustable ultrasonic focusing nozzle, and FIG. 23 is a principle diagram of spinning. As shown in FIG. 23, the spinning medium 4029 is a polymer solution or melt and is filled in an injection pump 4028, and a metal electrode 4030 is inserted into the spinning medium 4029. The electrode is connected with a high-voltage electrostatic generator 4027 to charge the liquid. The grounded receiving plate 4032 serves as a cathode. When the electric field is not activated, a constant thrust is applied to the piston by the syringe pump 4028, and the spinning medium 4029 in the syringe pump 4028 is extruded onto the needle at a fixed rate. When the high-voltage electric field is not turned on, the spinning solution forms droplets suspended from the nozzles under the synergistic action of gravity, self-viscosity and surface tension. When the electric field is turned on, charges are generated on the surface of the polymer solution, and the mutual repulsive charge and the opposite surface charge of the charge electrode generate a force opposite to the surface tension. When the voltage is not large enough, the surface tension of the surface of the droplet will prevent the droplets from being ejected while remaining at the nozzle. When the applied voltage increases, the hemispherical surface of the droplet to be dropped will be twisted into a cone, and the applied voltage will continue to increase. When the voltage exceeds a certain critical value, the charged portion of the solution overcomes the surface tension of the solution to form a charged jet, and the charged jet is ejected from the nozzle. Under the action of the electric field, when the fiber jet 4031 is stretched to a certain extent, the bending and further split stretching phenomena occur, at this time, the solvent is rapidly volatilized due to the rapid increase of the specific surface area of the jet 4031, and finally, the fiber jet is collected on a collection net and cured into a non-woven fabric fiber mat. The high-voltage electrostatic generator 4027 is usually supplied with a high voltage of 5 to 20 kV. In addition, the positive voltage field is beneficial to the release of charges on the surface of the fiber, while the negative voltage field provides a relatively stable electric field force, and the two have difference influence on electrostatic atomization film formation of different polymers.

The basic theory of electrospinning: After the charged droplets are introduced into the electric field, the charges accumulate on the surface of the droplets, thereby generating a charge repulsion (represented as electrostatic pressure $P_E=\sigma^2/2\varepsilon_0$ on the surface of the charged droplets, related to the density $\sigma$ of charges on the surface of the droplets and a dielectric constant $\varepsilon_0$ in vacuum) that drives the droplets to split outward. The charge repulsion and the surface tension (represented as $P_C=2\gamma/R$ related to the liquid surface tension $\gamma$ at the tail end of the nozzle and the radius R of the droplets) which tends to shrink the droplets on the surface of the droplets form an unsteady balance that can be expressed as:

$$\Delta P=2\gamma/R-e^2/(32\varepsilon_0\pi^2R^4) \quad (8)$$

In which, e is the total charges carried by the droplets; and R is the radius of the droplets.

It can be seen that as the radius of the droplets decreases (the charge density increases), the pressure generated by the static electricity increases. When the tension generated on the surface of the droplets is equal to the electrostatic repulsion, the charged droplets in the electric field achieve a balance. It is assumed that the diameter of the charged droplets is D, which is converted into the charge density on the surface of the droplets, the following equation can be obtained:

$$e/M=\sqrt{[(288\varepsilon_0\gamma)/(\rho^2D^3)]} \quad (9)$$

Wherein, M is the mass of a droplet.

When the charge repulsion exceeds this limit, the droplet at the end of the nozzle splits into a plurality of small droplets, forming an electrostatic atomization phenomenon. This limit of droplet stabilization is called "Rayleigh stability limit". If the liquid jet is cylindrical, the condition of "Rayleigh stability limit" can be expressed by the following equation:

$$\Delta P=\gamma/R-\tau^2/(8\varepsilon_0\pi^2R^4) \quad (10)$$

In which, $\tau$ indicates charges carried by a liquid jet length unit and is converted into the charge density of the jet surface as:

$$e/M=\sqrt{[(64\varepsilon_0\gamma)/(\rho^2D^3)]} \quad (11)$$

It can be seen from the above equation that when the condition of "Rayleigh stability limit" is satisfied, less charges are needed to form a cylindrical jet on the surface of a Taylor cone with respect to electrostatic atomization, and the special example is electrospinning.

The formula for calculating the critical voltage of the jet from the tip of the Taylor cone is:

$$V^2c=(4H^2/L^2)\cdot[\ln(2L/R)-1.5]\cdot(0.117\pi\gamma R_0) \quad (12)$$

In which: H is the distance between two electrodes; L is the distance that the nozzle extends out of a polar plate; R is the radius of a suspended droplet; $R_0$ is the radius of the nozzle.

The forces borne by the surface of the suspended droplet mainly include electric field force, viscous stress, hydrostatic pressure difference, and pressure difference caused by the surface tension. When the tangential electric field force on the surface of the suspended droplets is greater than the tangential viscous stress, a single jet or multiple jets are formed; otherwise, droplets are formed.

As shown in FIG. 2, an end cover I 101 and an end cover II 1022 play a role in axial positioning of bearings, dust proofing and sealing, and are respectively fixed on an electric spindle housing 103 by screws II 1035 and spring washers III 1036 as well as screws I 1025 and spring washers I 1024. Since the grinding device is at an angle to the horizontal direction during actual operation, a spindle 104 and a horn I 1017 bear axial and radial force, so a conical roller bearing II 1034 and a conical roller bearing I 1018 are adopted in the device. The conical roller bearing II 1034 is positioned by the end cover I 101 and the shoulders of the spindle 104, and the conical roller bearing I 1018 is positioned by the shoulders of the horn I 1017 and the end cover II 1022. The end cover II 1022 is sealed by a sealing ring 1023 to prevent leakage of lubricating oil, and can also prevent external dust from entering the electric spindle. In addition, the sealing ring 1023 can also reduce friction. Spacers I 102 and spacers II 1021 can adjust bearing clearances, the spindle 104 thermally expands during rotation, and the thermal elongation of the spindle is adjusted through the spacers. A stator winding 107 is integrated with the electric spindle housing 103. When a power interface I 105 is powered on, the stator winding 107 is energized under the conduction of a power line I 106 to generate a rotating magnetic field, current flows through a rotor winding 108 and the rotor winding 108 is rotated by the magnetic field. Since the spindle 104 is integrated with the rotor winding 108, the spindle 104 rotates. The spindle 104 is connected with a connecting cylinder 1011 through a coupling 109 and threaded holes I 1010 and rotates, and the connecting cylinder 1011 drives an electrode sheet I 1015, an electrode sheet II 1029, an electrode sheet III 1031, piezoelectric ceramic sheets I 1028 and the horn I 1017 to rotate through a center screw I 1033 and a spring washer II 1032.

FIG. 3 is a schematic diagram of part of an ultrasonic mechanism. The electrode sheet III 1031 and the electrode sheet II 1029 are led out from the connecting cylinder 1011 and then connected. During operation, the ultrasonic generator 5 converts alternating current into high-frequency electric oscillation signals, the high-frequency electric oscillation signals are respectively transmitted to the electrode sheet I 1015, the electrode sheet III 1031 and the electrode sheet II 1029 by a power interface II 1013 and a power line II 1014 through short brushes 1012 and long brushes 1030 fixed on a sleeve 1016, and the high-frequency electric oscillation signals are converted into an axial high-frequency vibration by the piezoelectric ceramic sheets I 1028. However, the amplitude of the vibration is relatively small, and cannot meet the amplitude requirement of skull grinding. Therefore, the lower end of the piezoelectric ceramic sheets I 1028 is tightly connected with the horn I 1017, thereby amplifying the amplitude. Finally, the amplified amplitude is transmitted to the grinding tool, causing the grinding tool to generate a vibration that meets the processing requirement.

FIG. 4 shows an exponential segment function of the horn. In the case of simple harmonic vibration, the wave equation of propagation of the longitudinal vibration in the variable section horn is:

$$\frac{\partial^2 \xi}{\partial x^2} + \frac{1}{S} \cdot \frac{\partial S}{\partial x} + k^2 \xi = 0 \quad (13)$$

In which: $\xi$ is a displacement function of longitudinal vibration; k is the number of circular waves, $k=\omega/c$, $\omega$ is an angular frequency, $c=\sqrt{E/\rho}$ is a propagation velocity of longitudinal waves in the horn; and E is a Young's modulus of a material.

As shown in FIG. 4, the horn has a cross-sectional area $S_1$ at the origin of coordinates (x=0), and has a cross-sectional area $S_2$ at x=1; and the forces and the vibration velocities of longitudinal waves acting on the input end (x=0) and the output end (x=1) of the horn are respectively $F_1$, $\xi_1'$ and $F_2$, $\xi_2'$. The function of the circular section radius of the exponential horn is:

$$R = R_1 e^{-\beta x} \quad (14)$$

In which:

$$\beta = \frac{1}{l}\ln\sqrt{\frac{S_1}{S_2}} = \frac{1}{l}\ln\frac{R_1}{R_2} = \frac{1}{l}\ln N,$$

N is an area function, $$N = \sqrt{\frac{S_1}{S_2}} = \frac{R_1}{R_2}.$$

The solution of equation (13) can be obtained as:

$$\xi = e^{\beta x}(a_1 \cos K'x + a_2 \sin K'x)e^{j\omega t} \quad (15)$$

In which, $K' = \sqrt{K^2 - \beta^2}$.

For the convenience of calculation, a time factor $e^{j\omega t}$ is omitted, and the expression of strain distribution is:

$$\frac{\partial \xi}{\partial x} = \beta e^{\beta x}(a_1 \cos K'x + a_2 \sin K'x)e^{j\omega t} + \quad (16)$$
$$e^{\beta x}(-a_1 K' \sin K'x + a_2 K' \cos K'x)$$

The boundary condition of the horn is free at two ends:

$$\begin{cases} x = 0 & \xi = \xi_1 & \xi_1' = \frac{\partial \xi}{\partial t}\bigg|_{x=0} & \frac{\partial \xi}{\partial x}\bigg|_{x=0} = 0 \\ x = l & \xi = -\xi_2 & \xi_2' = -\frac{\partial \xi}{\partial t}\bigg|_{x=l} & \frac{\partial \xi}{\partial x}\bigg|_{x=l} = 0 \end{cases} \quad (17)$$

According to the boundary condition (17) and equations (15) and (16), $a_1 = \xi_1$ and $$a_2 = -\frac{\beta}{K'}\xi_1$$

can be obtained, and substituted into equation (15) to obtain a displacement distribution equation of particles in the axial direction:

$$\xi = \xi_1 e^{\beta x}\left(\cos K'x - \frac{\beta}{K'}\sin K'x\right) \quad (18)$$

According to equation (18), obtained is:

$$\begin{cases} \xi|_{x=0} = \xi_1 \\ \xi|_{x=l} = \xi_1 e^{\beta l}\left(\cos K'l - \frac{\beta}{K'}\sin K'l\right) \\ M_P = \left|\frac{\xi|_{x=l}}{\xi|_{x=0}}\right| = e^{\beta l}\left(\cos K'l - \frac{\beta}{K'}\sin K'l\right) \end{cases} \quad (19)$$

A frequency equation $K'l = n\pi$ is substituted into equation (19) to obtain an amplification factor $M_P$ of the exponential horn:

$$M_P = e^{\beta l} = N \quad (20)$$

FIG. 5(a) and FIG. 5(b) are force analysis diagrams of rectangular spiral grooves of the horn I 1017. It can be seen from the diagrams that the force can be decomposed into an axial force $F_L$ and a tangential force $F_T$ through the spiral grooves, and the relationship between them is:

$$\begin{cases} F_L = F\cos\theta \\ F_T = F\sin\theta \end{cases} \quad (21)$$

In which: θ is the inclination angle of the spiral grooves.

It can be known from the theory of mechanical vibration that $F_T$ produces a torsional vibration and $F_L$ produces a longitudinal vibration. The torque M at the spiral grooves can be expressed as:

$$M = \int rf dS \quad (22)$$

In which: r is the distance from any point on the helical surface to the central axis; f is the tangential stress at any point on the helical surface; dS is a differential at r, and:

$$S = \pi r^2 - \pi (r - r_1)^2, \ r_1 < r < r_2 \quad (23)$$

In which: $r_1$ is the distance from the bottom of the spiral groove to the central axis; and $r_2$ is the distance from the top of the spiral groove to the central axis. Equation (23) is derived to obtain:

$$dS = 2\pi r_1 dr \quad (24)$$

Equation (24) is substituted into equation (22) to obtain:

$$M = \int_{r_1}^{r_2} r \frac{F\sin\theta}{2\pi r r_1 - \pi r_1^2} 2\pi r_1 dr \quad (25)$$

Equation (25) is integrated to obtain $$M = 2F\sin\theta\left(\frac{r_2}{2} - \frac{r_1}{2} - \frac{r_1}{4}\ln r_1 + \frac{r_1}{4}|2r_2 - r_1|\right) \quad (26)$$

It can be seen from equation (26) that the spiral grooves can not only produce a longitudinal vibration but also a torsional vibration, thereby realizing a longitudinal-torsional composite vibration of the horn. The spiral grooves may be rectangular spiral grooves or arc spiral grooves, or triangular, rectangular or trapezoidal fence group through slots, which can decompose the longitudinal waves to excite the torsional vibration. FIGS. 6(a) and 6(b) are cross-sectional views of a horn of triangular fence group through slots. A threaded hole at the upper end of the horn I 1017 is fastened with the center screw I 1033, a threaded hole at the lower end is fastened with the grinding tool handle 201, and the thread directions of the two threaded connections are opposite to the direction of rotation.

As shown in FIG. 7, the water-catching grinding tool 2 includes a grinding tool handle 201 and a grinding head base 202. FIG. 8 shows the upper part of the grinding tool handle 201. Threads are machined at the upper end of the grinding tool handle 201 and fastened with the threaded hole at the lower end of the horn I 1017.

FIG. 9 shows a wet state of droplets on a smooth flat surface, $\beta_e$ is an intrinsic contact angle of the droplets on the smooth flat surface (Young model), and FIGS. 10 and 11 show a wet state of droplets on a rough surface, respectively Wenzel and Cassie models.

The Wenzel model suggests that the actual solid-liquid contact area is greater than the apparent geometric contact area in the presence of a rough surface, which geometrically enhances the hydrophilicity (or hydrophobicity). As shown in FIG. 10, it is assumed that the groove structures on the surface are always full of droplets, the relationship between the apparent contact angle β* of the rough surface and $\beta_e$ is:

$$\cos \beta^* = r(\gamma_{SG} - \gamma_{SL})/\gamma_{LG} = r\cos\beta_e \quad (27)$$

In which: $\gamma_{SG}$, $\gamma_{SL}$ and $\gamma_{LG}$ are respectively surface tension of solid-gas, solid-liquid, and liquid-gas contact surfaces; r is a surface roughness factor of a material and is the ratio of the actual contact area to the apparent contact area, r≥1. Therefore, the apparent contact angle can be adjusted by changing the solid surface roughness so as to change the wettability of the solid surface.

As shown in FIG. 11, in the Cassie model, the contact of the droplets on the rough surface is regarded as a composite contact, the grooves in the rough surface cannot be full of the droplets, and trapped air is present under the droplets in the grooves, so that the apparent liquid-solid contact is actually composed of liquid-solid and gas-solid contacts thermodynamically:

$$dG = f_s(\gamma_{SL} - \gamma_{SG})dx + (1-f_s)\gamma_{LG} dx + \gamma_{LG} dx \cos \beta^* \quad (28)$$

When the droplets are balanced, the apparent contact angle β* of the rough surface is a mean of the intrinsic contact angles $\beta_e$ of the smooth flat surface and 180°:

$$\cos \beta^* = f_s(1 + \cos \beta_e) - 1 \quad (29)$$

In which: $f_s$ is an area fraction ($f_s < 1$) of raised solids in the composite contact surface. A three-phase contact boundary is the most important factor affecting the dynamic behavior of surface droplets. As shown in FIG. 12, when the droplets are balanced, the contact angle is β (state d); when a small amount of liquid is added, the solid-liquid-gas three-phase contact boundary remains stationary, and the contact angle is necessarily increased to $\beta_2$ (state e); conversely, if a small amount of liquid is drawn while the solid-liquid-gas three-phase contact boundary is kept stationary, the contact angle is necessarily reduced to $\beta_1$ (state c). It is assumed that the solid-liquid-gas three-phase contact boundary has only three interfacial tensions. When balanced, states d, e and c are:

$$\cos\beta = \cos\beta_1 = \cos\beta_2 = \frac{\gamma_{SG} - \gamma_{SL}}{\gamma_{LG}} \quad (30)$$

Figures 13, 14:
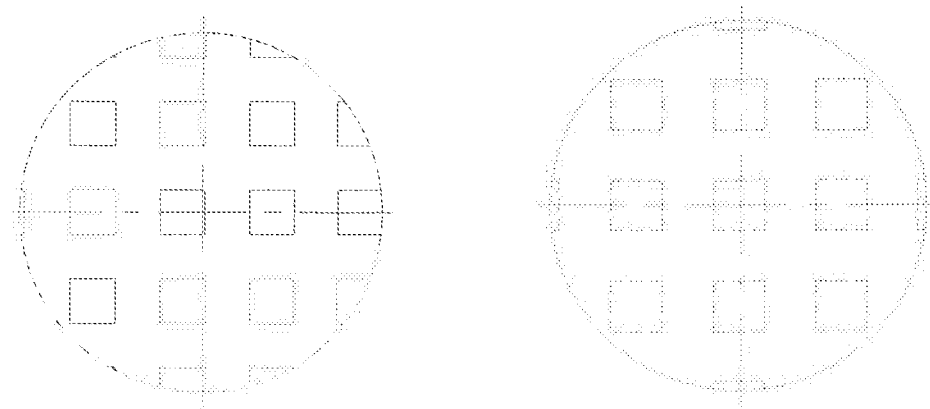

If the droplets at the balanced spread position continue to spread along the solid wall, it is necessary to overcome the pinning effect of the solid on the contact boundary. During the cooling process of neurosurgical skull grinding, a coolant continuously flows into the grinding zone. The previous coolant droplet impacts on the surface of the bone at certain speed and angle and is spread into a liquid film. The most favorable status for the cooling and lubrication effect is that the subsequent droplet impacts on the position of the previous droplet and is continuously spread, i.e., the coolant droplets can overcome the pinning effect of the rough bone surface on the contact boundary. The dashed lines in FIGS. 13 and 14 are solid-liquid-gas three-phase contact boundaries of droplets in Wenzel and Cassie wet states, respectively. It can be seen from the figures that the three-phase contact boundary of droplets in the Wenzel model is long and continuous, while the three-phase contact boundary of droplets in the Cassie model is short and discontinuous. When the three-phase contact boundary is long and continuous, the energy barrier of the droplets continuously spread along the solid wall is low, and the three-phase contact boundary is prone to pinning-de-pinning transformation, so the spreading characteristic is good; when the three-phase contact boundary is short and discontinuous, the droplets are obvious in lag effect and poor in spreading characteristic.

Since the hydrophilicity/hydrophobicity of the surface of human skull to coolant droplets is unknown and uncontrollable, the grinding tool can be designed with microstructures on the surface to have a water-catching property, thereby improving the cooling and lubricating performance of the medical nanofluid droplets. Based on the analysis on the wet state of the coolant droplets and the solid-liquid-gas three-phase contact boundary, it can be seen that after the droplets impact on the microstructure surface of the grinding tool, the droplets can be spread at small contact angles and can overcome the pinning effect of the grinding tool on the contact boundary, i.e., the wet state of the droplets is closer to the Wenzel model, and the microstructure surface is the most favorable surface for cooling and lubrication of skull grinding. A micro-bulge structure is more advantageous than a micro-pit structure to prevent the Wenzel/Cassie wet state transition, and is more suitable for manufacturing the water-catching grinding tool.

Figure 15:
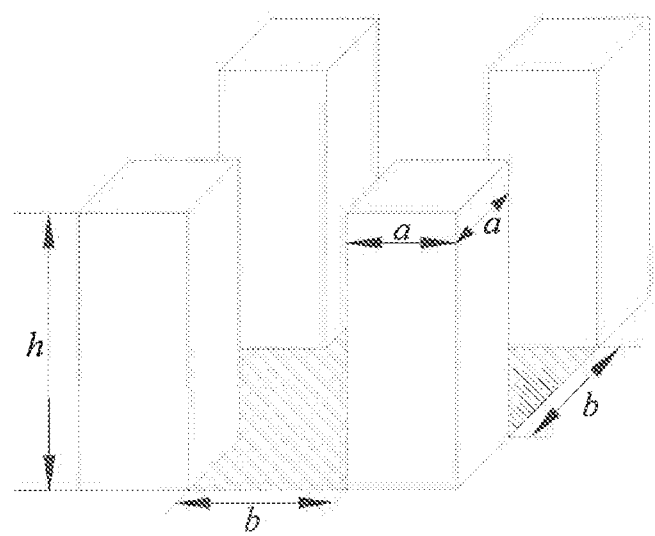

FIG. 15 shows a surface dimension diagram of square cylindrical bulge microstructures, in which the size of a micro-bulge is a×a, the height is h, the spacing between the micro-bulges is b, the roughness factor r and the area fraction $f_s$ occupied by the protruding solids in the contact surface are:

$$\begin{cases} r = \dfrac{(a+b)^2 + 4ah}{(a+b)^2} \\ f_s = \dfrac{a^2}{(a+b)^2} \end{cases} \quad (31)$$

Two three-dimensional surface characteristic values are introduced: $\sigma = b/a$, $\tau = h/a$. Equation (31) is substituted into (27) and (29) to obtain:

$$\cos\beta^* = r\cos\beta_e = \frac{(a+b)^2 + 4ah}{(a+b)^2}\cos\beta_e \quad (32)$$

$$\cos\beta^* = f_s(1+\cos\beta_e) - 1 = \frac{a^2}{(a+b)^2}(1+\cos\beta_e) - 1 = \frac{1+\cos\beta_e}{(1+\beta)^2} - 1 \quad (33)$$

It can be seen from equation (32) that for the Wenzel model, when σ is constant, the hydrophobic material is more hydrophobic and the hydrophilic material is more hydrophilic by improving τ, when τ is constant, the hydrophobic material is more hydrophobic and the hydrophilic material is more hydrophilic by reducing σ.

It can be seen from equation (33) that for the Cassie model, when a hydrophobic material has certain $\beta_e$ (>90°), if the hydrophobic property of the material is to be improved (i.e., larger β*), a should be larger, when the hydrophilic material has certain $\beta_e$ (<90°), if the hydrophilic property of the material is to be improved (i.e., smaller β*), σ should be smaller.

Figure 16:
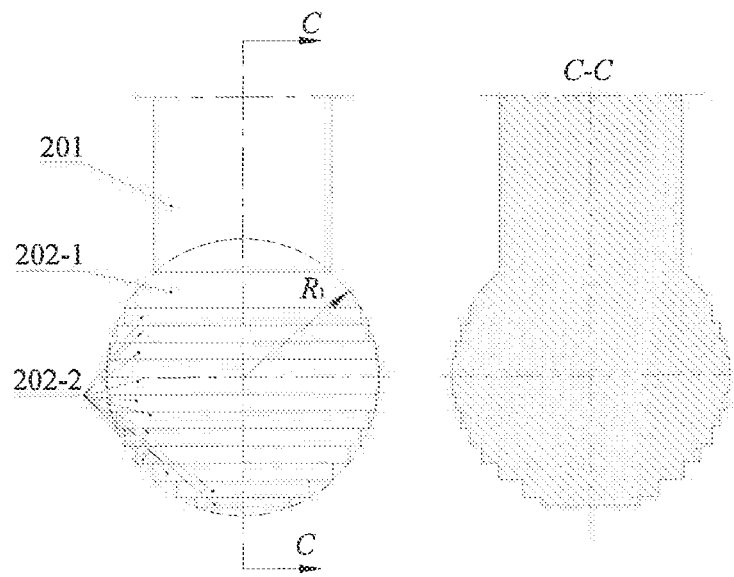

A neurosurgical skull grinding water-catching grinding tool is designed based on the above analysis. The grinding tool is made of 420b or 630 stainless steel, which is the most widely used material in present clinical skull surgery, and the Young's contact angle between the material and water-based liquid is 85°, that is, the material itself has weak hydrophilicity, and is more favorable for preparing a super-hydrophilic surface. FIG. 16 shows a grinding head base of the water-catching grinding tool and a cross-sectional view. As shown in FIG. 16, the grinding head base 202 is composed of eleven octagonal cylinders 202-2 and a partial sphere 202-1, the octagonal cylinders 202-2 are spliced vertically in sequence, the partial sphere 202-1 is arranged at the top of the octagonal cylinders and connected with the grinding tool handle 201, and the edges of the octagonal cylinders and the partial sphere are distributed on a circle having a radius $R_1$.

Figure 17A:
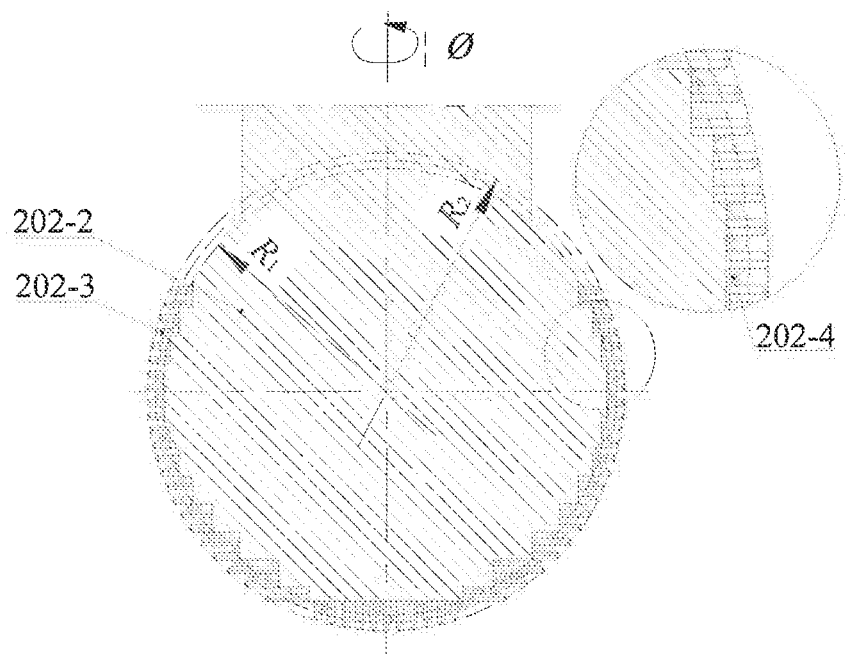
Figure 17B:
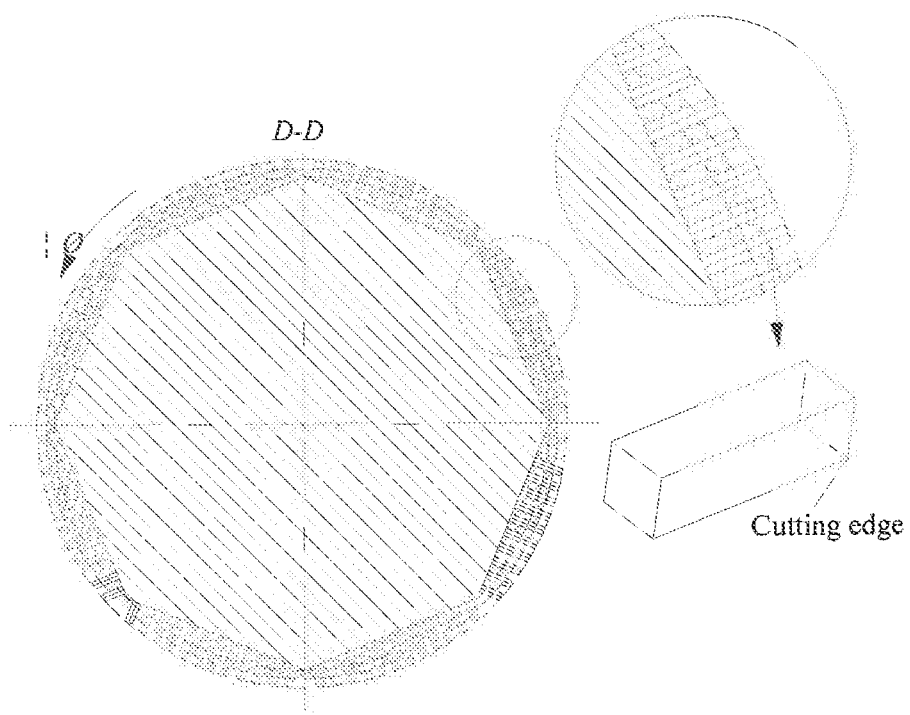

It can be known from equation (32) that when the side length and spacing of the micro-bulges are constant, the nanofluid droplets can be more hydrophilic by improving the height of the micro-bulges. The microstructure of the grinding head base is designed as shown in FIG. 17(a) and FIG. 17(b), the rotation speed of the grinding tool is ω, square cylindrical micro-bulges 202-3 are uniformly distributed on each octagonal cylinder, and the edges of the bulges 202-3 are distributed on a circle having a radius $R_2$. The micro-bulges 202-3 having a feature size of micron-scale also serve as abrasive grains to cut the bone material while adhering nanofluid droplets, and the edges of the square columns are cutting edges. The micro-bulges are arranged on the surface of the base by soldering.

An aqueous dispersion of a water-soluble polymer and a water-insoluble polymer is applied to the 420b (or 630) stainless steel surface by drop casting and dried. During the drying process, the water-soluble polymer and the water-insoluble polymer undergo phase separation to form a nano separator on the 420b stainless steel and form a non-nano separator film on the nano separator. The non-nano separator film is washed away with deionized water to obtain a nano separator film 202-4. Due to the intermolecular rearrangement, the nano separator film 202-4 is tightly adhered between the micro-bulges 202-3 on the surface of the grinding head base 202. The nano separator film 202-4 has super-hydrophilic property and strong water catching ability. Therefore, the nano separator film 202-4 having a nano thickness can convert the 420b stainless steel surface into a super-hydrophilic surface while having a property of capturing a medical nanofluid coolant water film.

FIG. 1 is a schematic diagram of a low-damage and controllable biotic bone grinding device, including a longitudinal torsional resonant rotary ultrasonic electric spindle 1, a water-catching grinding tool 2, an endoscope 3, a focus adjustable ultrasonic focusing assisted three-stage atomization cooling and film forming mechanism 4, an ultrasonic generator 5, a fluid storage cup 6 and an ultrasonic vibration bar 7. The longitudinal torsional resonant rotary ultrasonic electric spindle 1 can realize longitudinal-torsional and rotary motions of horns, and the water-catching grinding tool 2 installed can remove pathological bone tissues safely and efficiently with the aid of the endoscope 3; the cooling and film forming mechanism 4 performs pneumatic-ultrasonic-electrostatic three-stage atomization on a medical nanofluid, and the nanofluid is finally flushed to a grinding zone in the form of droplets under the action of ultrasonic focusing for effective cooling and lubrication; at the same time, the nanofluid coats the postoperative wound to prevent wound infection; the ultrasonic vibration bar 7 can ultrasonically oscillate the medical nanofluid (or medical spinning medium) in the fluid storage cup 6 to prevent agglomeration of nanoparticles (reduce the viscosity of the spinning medium). The longitudinal torsional resonant rotary ultrasonic electric spindle 1, the cooling and film forming mechanism 4 and the ultrasonic vibration bar 7 share one ultrasonic generator 5.

As shown in FIG. 19, when a medical nanofluid is stored in the fluid storage cup 6, the nanofluid can be pneumatically and ultrasonically atomized and then electro-statically atomized to obtain superfine droplets distributed uniformly for effectively cooling and lubricating the grinding zone. When an electrospinning system applied to wound dressing is stored in the fluid storage cup 6, superfine fibers can be obtained in the same way to coat a postoperative wound. FIG. 24 shows a fluid path and gas path system of the device. The fluid path (nanofluid) of the cooling and film forming mechanism is composed of a fluid storage cup I 608, a hydraulic pump I 609, a pressure regulating valve II 6011, a throttle valve II 6016 and a turbine flow meter II 6017 connected in sequence; the fluid path (spinning medium) of the film forming device is composed of a fluid storage cup II 6012, a hydraulic pump II 6013, a pressure regulating valve III 6015, a throttle valve II 6016 and a turbine flow meter II 6017 connected in sequence; and the gas path is composed of an air compressor 601, a filter 602, a gas tank 603, a pressure regulating valve I 605, a throttle valve I 606 and a turbine flow meter I 607 connected in sequence. During operation, the hydraulic pump is started, and the fluid stored in the fluid storage cup enters a nanofluid inlet 4013-13 of the nozzle body 4013-2 via the fluid pressure regulating valve, the fluid throttle valve and the turbine flow meter. The overflow valve 6019 functions as a safety valve. When the pressure in the fluid path exceeds a set pressure, the overflow valve 6019 is opened to allow the coolant to flow back to a recycling tank 6018 via the overflow valve 6019. The nanofluid (or spinning medium) flows out of the turbine flow meter II 6017 and then enters the fluid inlet pipe 407 (FIG. 18), enters the internal nanofluid inlet 4013-13 (FIG. 20) of the nozzle body via the internal liquid inlet channel II 4014 (FIG. 19) of the horn II 4014, and is ejected from the nozzle body 4013-2 after three-stage atomization.

When the hydraulic pump is started, the air compressor 601 is started, high pressure gas enters the compressed gas inlet 4013-14 of the nozzle body 4013-2 via the filter 602, the gas tank 603, the gas pressure regulating valve I 605, the gas throttle valve I 606 and the gas turbine flow meter I 607, and a pressure gauge 604 monitors the pressure value in the gas path. The compressed gas flows out of the turbine flow meter I 607 and then enters the air inlet pipe 408 (FIG. 18), enters the internal compressed gas inlet 4013-14 (FIG. 20) of the nozzle body via the internal air inlet channel 4014-2 (FIG. 19) of the horn II 4014, and is mixed with the nanofluid, and the mixture is ejected from the nozzle body 4013-2.

During the operation, the reversing valve II 6014 is at a normal position, the fluid path of the fluid storage cup II 6012 is not opened; the reversing valve I 6010 is at a working position, and the fluid path of the fluid storage cup I 608 works normally; after the operation is finished, the reversing valve I 6010 is closed, the reversing valve II 6014 is opened, and the fluid path of the fluid storage cup II 6012 works. The pressure and flow rate of the nanofluid (or spinning medium) and the high-pressure gas can achieve an optimal micro-lubrication effect as needed by adjusting the pressure regulating valves, the throttle valves and the flow meters in the gas path and the liquid path.

As shown in FIG. 25, one end of a connecting rod 4038 is welded on the top cover I 403, and the other end is welded on the connecting plate III 4037. The electric spindle housing 103 is machined with a threaded hole IV 1026 and a threaded hole V 1027. The cooling and film forming mechanism is fixed on the electric spindle housing 103 by screws VIII 4033, spring washers X 4034, screws IX 4035, spring washers XI 4036, connecting plates III 4037 and connecting rods 4038.

FIG. 26 is a half cross-sectional view of the ultrasonic vibration bar. A top cover II 703, piezoelectric ceramic sheets III 709, an electrode sheet VII 706, an electrode sheet VIII 7010 and an electrode sheet IX 7012 are fastened and connected by a center screw III 7014 and a spring washer XIII 7013, and a transducer housing 704 is fixed on the top cover II 703 via screws X 701 and spring washers XII 702. During operation, the ultrasonic generator 5 converts alternating current into high-frequency electric oscillation signals, the high-frequency electric oscillation signals are transmitted to the electrode sheet VII 706, the electrode sheet VIII 7010 and the electrode sheet IX 7012 through an electric excitation signal line IV 705 and an electric excitation signal line V 7011 respectively and converted into an axial high-frequency vibration, and the amplitude is amplified by a horn III 707. The horn III 707 is fastened with a vibration bar 708 by threads, and transmits the amplified vibration to the vibration bar 708 to ultrasonically oscillate the medical nanofluid (or medical spinning medium) in the fluid storage cup 6.

The ultrasonic vibration bar 7 performs ultrasonic oscillation on the spinning system in the fluid storage cup 6, thereby effectively reducing the viscosity of the electrospinning solution and melt, expanding the electrospinning concentration range of the device, effectively reducing the diameters of fibers and the structural defects of the fibers, and improving the mechanical properties of the spinning fibers. Ultrasonic waves of certain power are applied during fiber formation by using the ultrasonic focusing device shown in FIG. 21, so that the fibers can be stretched under the action of jet flow to achieve the purpose of further thinning, at the same time, the ultrasonic effect can improve the fluidity of the polymer solution, improve the spinnability and accelerate the process of solidification of the fibers.

The longitudinal torsional resonant rotary ultrasonic electric spindle 1 realizes longitudinal-torsional and rotary motions of horns, and the water-catching grinding tool 2 installed can remove pathological bone tissues safely and efficiently with the aid of the endoscope 3; the cooling and film forming mechanism 4 performs pneumatic-ultrasonic-electrostatic three-stage atomization on the nanofluid, and the nanofluid is finally flushed to the grinding zone in the form of droplets under the action of ultrasonic focusing for effective cooling and lubrication; and at the same time, the nanofluid coats the postoperative wound to prevent wound infection.

Figure 27:
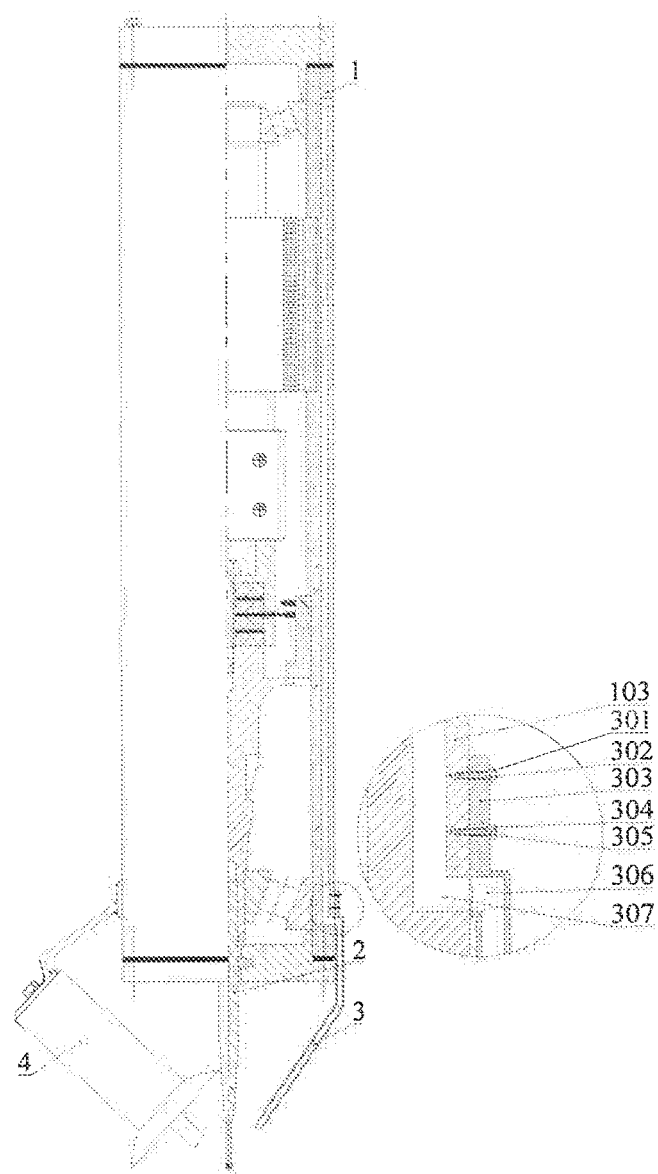
Figure 28:
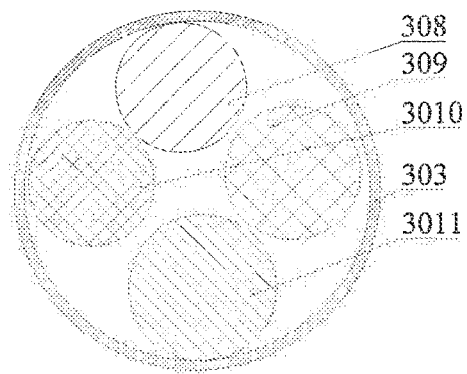

FIG. 27 shows an installation diagram of the endoscope in the electric spindle housing. The electric spindle housing 103 is machined with a threaded hole II 1019 and a threaded hole III 1020. The endoscope body 303 is fixed on the electric spindle housing 103 by a screw III 301, a spring washer IV 302, a screw IV 304 and a spring washer V 305. A fiber channel II 307 is provided inside the electric spindle housing 103, and a fiber channel I 306 is provided inside the endoscope body 303. FIG. 28 shows a cross-sectional view of the interior of 303. A cold light illumination source transmission fiber 308, an endoscope fiber 309, a fluorescence excitation light transmission fiber 3010 and an image transmission fiber 3011 independent from one another are arranged in the endoscope. The fluorescence excitation light can excite tumor tissues to emit fluorescence of corresponding wavelengths, the fluorescence emitted light passes through the endoscope fiber 309 and the image transmission fiber 3011, and the fluorescence emitted light can be seen through an eyepiece, so that tumor tissues are accurately identified. The image transmission fiber 3011 is connected to a monitor, thereby facilitating excision of identifiable tissues with surgical instruments under the illumination of the fiber to achieve the purpose of therapy. Since the endoscope 3 is closely connected with the longitudinal torsional resonant rotary ultrasonic electric spindle 1, a surgeon can conveniently and flexibly realize the operation of any posture in real time with the aid of the endoscope 3, and realize flexible removal of skull base tumors.

The Specific Working Process of this Solution is as Follows:

A neurosurgical ultrasonic focusing assisted three-stage atomization cooling and postoperative wound film forming device, wherein the longitudinal torsional resonant rotary ultrasonic electric spindle 1 can realize longitudinal-torsional and rotary motions of the grinding tool, which is beneficial to timely discharge of bone debris and achieves high grinding efficiency; the grinding tool is a water-catching grinding tool 2, square cylindrical micro-bulges are regularly arranged on the grinding head, and the surface of the grinding head base is treated to obtain a nano separator film with strong water-catching ability and super hydrophilicity, thereby enhancing the convective heat exchange in the grinding zone; the cooling and film forming mechanism 4 performs pneumatic-ultrasonic-electrostatic three-stage atomization on the medical nanofluid coolant to obtain superfine droplets, and the nanofluid droplets are injected into the grinding tool/bone wedge-shaped constraint space by ultrasonic focusing to effectively cool and lubricate the grinding zone; and after the operation, the spinning system applied to wound dressing is sprayed onto the postoperative wound surface in the form of spinning fibers after three-stage atomization to achieve atomized film forming protection on the ground wound surface. Removal of skull base tumors under the endoscope, intraoperative cooling and postoperative wound film formation can be implemented using one device with high integration, high grinding removal efficiency and low grinding temperature, that is, low-damage and controllable grinding on a biotic bone can be implemented using one device.

When the device is used, the conical roller bearing II 1034 is positioned by the end cover I 101 and the shoulders of the spindle 104, and the conical roller bearing II 1034 is installed at one end of the spindle 104 by the positioning device. The electrode sheets and the piezoelectric ceramic sheets are installed in the connecting cylinder 1011 by the center screw I 1033 and the spring washer II 1032, and the connecting cylinder 1011 is connected with the spindle 104 through the coupling 109 and the threaded hole I 1010. The end covers play a role in axial positioning of bearings, dust proofing and sealing. The end cover I 101 is installed at the top of the electric spindle housing 103 through the spring washers III 1036 and the screws II 1035, the spindle 104 and the connecting cylinder 1011 assembled are installed within the electric spindle housing 103 according to the positions, and the sleeve 1016 is installed within the electric spindle housing 103 according to the position. The conical roller bearing I 1018 is positioned by the shoulders of the horn I 1017 and the end cover II 1022, the conical roller bearing I 1018 is installed at one end of the horn I 1017 according to the position, and the prepared water-catching grinding tool 2 is installed at the end of the horn I 1017 by threaded connection. The horn I 1017 is connected with the end of the center screw I 1033 in the electric spindle housing 103 through the threaded hole in the top of the horn I 1017. After being coated with lubricating grease, the end cover II 1022 is installed at the end of the electric spindle housing 103 by the screws I 1025 and the spring washers I 1024. The threaded hole at the upper end of the horn I 1017 is fastened with the center screw I 1033, the threaded hole at the lower end is fastened with the grinding tool handle 201, and the thread directions of the two threaded connections are opposite to the direction of rotation, thereby ensuring the connection tightness.

8, 16, 24, 32 and 40 uniform circular holes are respectively machined on concentric circles $r_1$, $r_2$, $r_3$, $r_4$ and $r_5$ around the center of the spherical crown transducer housing 404, plane wafer piezoelectric elements 4011 are nested and adhered in the circular holes, and all of the plane wafer piezoelectric elements 4011 have the same diameter and thickness. The copper mesh common electrode 4012 is adhered to the lower ends of all the plane wafer piezoelectric elements 4011 with an adhesive, and the bottom surface of the spherical crown portion is pressed by a pressure table, so that the adhered ends of the copper mesh common electrode 4012 and the plane wafer piezoelectric elements 4011 are flattened. The electrostatic atomizing nozzle 4013 is installed at the end of the horn II 4014 by screws VI 4022, spring washers VIII 4023, screws VII 4024, spring washers IX 4025 and a connecting plate I 4021. The spherical crown transducer housing 404, the electrode sheet V 4016, the piezoelectric ceramic sheets II 4015, the electrode sheet VI 4018 and the electrode sheet IV 406 constitute a transducer. The top cover I 403, the electrode sheets and the piezoelectric ceramic sheets are sequentially stacked, then installed on the transducer together with the horn II 4014 through the center screw II 401 and the spring washer VI 402, and fastened by the spring washers VII 4020 and the screws V 4019. The electric excitation signal lines II 4010, the fluid inlet pipe 407, the air inlet pipe 408 and the high voltage wire 409 are respectively connected to the corresponding positions, and finally, the assembled cooling and film forming mechanism is welded to the electric spindle housing 103 by the connecting rod 4038.

Before an operation, the power interface I 105, the power interface II 1013 and the ultrasonic generator 5 are simultaneously started. When the water-catching grinding tool 2 achieves stable rotation and longitudinal torsional vibration, the reversing valve I 6010 is opened, the cooling and film forming mechanism works, the medical nanofluid is ejected from the nozzle body 4013-2 in the form of droplet jet and enters the grinding zone for efficient cooling and lubrication, the endoscope system 3 is opened, and the surgery begins with the aid of the endoscope. After the grinding is completed, the reversing valve I 6010 is closed, the reversing valve II 6014 is opened, the film forming device works, and the postoperative wound is coated with spinning fibers. After the operation, all power is turned off, the water-catching grinding tool 2 is detached, and the device is disinfected and kept in a safe place.

Described above are merely preferred embodiments of the present application, and the present application is not limited thereto. Various modifications and variations may be made to the present application for those skilled in the art. Any modification, equivalent substitution, improvement or the like made within the spirit and principle of the present application shall fall into the protection scope of the present application.

The invention claimed is:

1. A neurosurgical ultrasonic focusing assisted three-stage atomization cooling and postoperative wound film forming device, comprising:

a transducer housing, wherein a horn II is arranged in the transducer housing, at least two layers of piezoelectric ceramic sheets II are arranged at a top of the horn II, an electrode sheet connected with an ultrasonic generator is arranged between two adjacent layers of piezoelectric ceramic sheets II, a bottom of the transducer housing is of a hemispherical structure, a plurality of piezoelectric elements connected with the ultrasonic generator are arranged inside the hemispherical structure, a copper mesh common electrode is arranged on a surface of the piezoelectric elements, and a bottom of the horn II protrudes from the hemispherical structure of the transducer; and a nozzle, arranged at the bottom of the horn II, wherein the nozzle is connected with a medical nanofluid storage cup, compressed gas can be introduced into the nozzle, an electrode is also arranged inside the nozzle, so after pneumatic-ultrasonic-electrostatic atomization medical nanofluid can be flushed into a grinding zone in a form of nanofluid droplet jet for effective cooling and lubrication, at the same time, a postoperative wound can be coated effectively.

2. The neurosurgical ultrasonic focusing assisted three-stage atomization cooling and postoperative wound film forming device according to claim 1, wherein (i) a liquid inlet channel and an air inlet channel are arranged inside the horn II, the liquid inlet channel communicates with a nanofluid inlet of the nozzle, and the air inlet channel communicates with a compressed gas inlet of the nozzle, or (ii) the electrode is connected with an external high-voltage electrostatic generator.

3. The neurosurgical ultrasonic focusing assisted three-stage atomization cooling and postoperative wound film forming device according to claim 2, wherein a nanofluid channel and a compressed gas channel are arranged in the nozzle, an internal compressed gas channel communicating with the nanofluid channel is also arranged in the nozzle, an acceleration chamber is arranged at the a bottom of the nanofluid channel, the compressed gas channel communicates with the acceleration chamber, and the internal compressed gas channel enters the nanofluid channel through a swirling compressed gas channel.

4. The neurosurgical ultrasonic focusing assisted three-stage atomization cooling and postoperative wound film forming device according to claim 3, wherein the acceleration chamber comprises a first communicating reducing section and a second communicating reducing section, the first communicating reducing section and the second communicating reducing section both have a shape of a reverse circular truncated cone, the second communicating reducing section is connected with a third section through a cylinder section, and the third section is a vortex chamber.

5. The neurosurgical ultrasonic focusing assisted three-stage atomization cooling and postoperative wound film forming device according to claim 1, wherein the piezoelectric elements are arranged on a circumference of a plurality of concentric circles.

6. A low-damage and controllable biotic bone grinding device, comprising:

the neurosurgical ultrasonic focusing assisted three-stage atomization cooling and postoperative wound film forming device according to claim 1;

a spindle, arranged in an electric spindle housing, wherein a rotor winding is arranged on a circumference of an outer surface of the spindle, a stator winding corresponding to the rotor winding is arranged in the electric spindle housing, and the stator winding can be energized to drive the spindle to rotate; and a water-catching grinding tool for grinding a biotic bone, wherein the spindle is connected with the water-catching grinding tool through an ultrasonic vibrator, the water-catching grinding tool achieves longitudinal-torsional and rotary motions under a drive of the spindle and the ultrasonic vibrator, and a surface of the water-catching grinding tool is provided with micro-bulges.

7. The low-damage and controllable biotic bone grinding device according to claim 6, further comprising an endoscope, wherein an endoscope body is fixed to the electric spindle housing, and an endoscope lens is arranged on one side of the water-catching grinding tool.

8. The low-damage and controllable biotic bone grinding device according to claim 6, wherein (i) the ultrasonic vibrator comprises four layers of piezoelectric ceramic sheets I, an electrode sheet connected with an ultrasonic generator is arranged between two adjacent layers of piezoelectric ceramic sheets I, and a bottom piezoelectric ceramic sheet I is connected with a top of the water-catching grinding tool through a horn I, or (ii) a surface of the horn I is provided with rectangular spiral grooves.

9. The low-damage and controllable biotic bone grinding device according to claim 6, wherein an end cover is respectively arranged at a top and a bottom of the electric spindle housing, and the water-catching grinding tool penetrates through the bottom end cover.

10. The low-damage and controllable biotic bone grinding device according to claim 6, wherein the water-catching grinding tool comprises a grinding tool handle, a spherical grinding head base is arranged at a bottom of the grinding tool handle, the spherical grinding head base comprises a partial sphere, a plurality of octagonal cylinders are arranged on a surface of the partial sphere, the octagonal cylinders are connected up and down in turn, a plurality of square cylindrical micro-bulges are arranged on a surface of the octagonal cylinders, and a nano-separator film is adhered among the micro-bulges on the surface of the octagonal cylinders.

* * * * *